US010835638B2

(12) United States Patent
Delaney, Jr. et al.

(10) Patent No.: US 10,835,638 B2
(45) Date of Patent: Nov. 17, 2020

(54) PHOTOCROSSLINKED POLYMERS FOR ENHANCED DURABILITY

(71) Applicant: Cardiac Pacemakers, Inc., St. Paul, MN (US)

(72) Inventors: Joseph T. Delaney, Jr., Minneapolis, MN (US); David R. Wulfman, Minneapolis, MN (US); Patrick Willoughby, Shoreview, MN (US); Andrew J. Ro, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 85 days.

(21) Appl. No.: 16/104,069

(22) Filed: Aug. 16, 2018

(65) Prior Publication Data
US 2019/0054204 A1    Feb. 21, 2019

Related U.S. Application Data

(60) Provisional application No. 62/547,059, filed on Aug. 17, 2017.

(51) Int. Cl.
*C08G 18/32* (2006.01)
*C09D 175/04* (2006.01)
(Continued)

(52) U.S. Cl.
CPC .............. *A61L 27/18* (2013.01); *C08G 18/12* (2013.01); *C08G 18/2825* (2013.01);
(Continued)

(58) Field of Classification Search
CPC .. C08G 18/12; C08G 18/025; C08G 18/2825; C08G 18/6674; C08G 18/3215;
(Continued)

(56) References Cited

U.S. PATENT DOCUMENTS 3,069,236 A    12/1962  Schultz et al.
3,148,028 A    9/1964   Schultz et al.
(Continued)

FOREIGN PATENT DOCUMENTS

BR    9003841 A     2/1992
CA    2278680 A1    8/1998
(Continued)

OTHER PUBLICATIONS

Muller, J.P. et al., "Surface modification of polyurethanes by multicomponent polyaddition reaction", Journal of Materials Science Letters 17(2), 1998, pp. 115-118.
(Continued)

*Primary Examiner* — Sanza L. McClendon
(74) *Attorney, Agent, or Firm* — Faegre Drinker Biddle & Reath LLP

(57) ABSTRACT

A block copolymer including a plurality of polymeric chains and a plurality of cross-linking compound residues linking together the plurality of polymeric chains. The plurality of polymeric chains forms a plurality of hard domains and a plurality of soft domains. Each polymeric chain includes a plurality of soft segments and a plurality of hard segments. The plurality of soft segments includes a polyisobutylene diol or diamine residue. The plurality of soft segments forms the plurality of soft domains. The plurality of hard segments including a diisocyanate residue. The plurality of hard segments forms the plurality of hard domains. The cross-linking compound residues link together the hard segments of the plurality of polymeric chains.

17 Claims, 7 Drawing Sheets

(51) Int. Cl.
| | | |
|---|---|---|
| *A61L 27/18* | (2006.01) | |
| *C08G 18/28* | (2006.01) | |
| *C08G 18/66* | (2006.01) | |
| *C08G 18/76* | (2006.01) | |
| *C08G 18/12* | (2006.01) | |
| *C08G 18/48* | (2006.01) | |
| *C08G 81/02* | (2006.01) | |
| *C08J 3/24* | (2006.01) | |

(52) U.S. Cl.
CPC ..... *C08G 18/3215* (2013.01); *C08G 18/4854* (2013.01); *C08G 18/6674* (2013.01); *C08G 18/7671* (2013.01); *C08G 81/025* (2013.01); *C08J 3/24* (2013.01); *C09D 175/04* (2013.01); *C08J 2375/04* (2013.01)

(58) Field of Classification Search
CPC ..... C08G 18/4854; C08J 3/24; C08J 3275/04; A61L 27/18
See application file for complete search history.

(56) References Cited

U.S. PATENT DOCUMENTS

| | | |
|---|---|---|
| 3,328,372 A | 6/1967 | Thomas et al. |
| 3,427,366 A | 2/1969 | Verdol et al. |
| 3,505,252 A | 4/1970 | Brotherton et al. |
| 3,642,964 A | 2/1972 | Rausch et al. |
| 3,755,265 A | 8/1973 | Fletcher et al. |
| 3,815,611 A | 6/1974 | Denniston, III |
| 4,043,331 A | 8/1977 | Martin et al. |
| 4,103,079 A | 7/1978 | Thaler |
| 4,118,427 A | 10/1978 | Rhein et al. |
| 4,154,913 A | 5/1979 | Hergenrother et al. |
| 4,157,429 A | 6/1979 | Hergenrother et al. |
| 4,157,430 A | 6/1979 | Hergenrother et al. |
| 4,276,394 A | 6/1981 | Kennedy et al. |
| 4,316,973 A | 2/1982 | Kennedy |
| 4,342,849 A | 8/1982 | Kennedy |
| 4,352,359 A | 10/1982 | Larimore et al. |
| 4,423,185 A | 12/1983 | Matsumoto et al. |
| 4,477,604 A | 10/1984 | Oechsle, III |
| 4,484,586 A | 11/1984 | McMickle et al. |
| 4,486,572 A | 12/1984 | Kennedy |
| 4,539,996 A | 9/1985 | Engel |
| 4,570,270 A | 2/1986 | Oechsle, III |
| 4,675,361 A | 6/1987 | Ward |
| 4,686,137 A | 8/1987 | Ward, Jr. et al. |
| 4,752,626 A | 6/1988 | Hoye et al. |
| 4,767,885 A | 8/1988 | Kennedy |
| 4,771,082 A | 9/1988 | Solodovnik et al. |
| 4,861,830 A | 8/1989 | Ward |
| 4,880,883 A | 11/1989 | Grasel et al. |
| 4,888,389 A | 12/1989 | Kennedy et al. |
| 4,906,673 A | 3/1990 | Mori |
| 4,910,321 A | 3/1990 | Kennedy et al. |
| 4,928,689 A | 5/1990 | Hauser |
| 4,939,184 A | 7/1990 | Kennedy |
| 5,000,875 A | 3/1991 | Kolouch |
| 5,017,664 A | 5/1991 | Grasel et al. |
| 5,026,814 A | 6/1991 | Re et al. |
| 5,029,585 A | 7/1991 | Lieber et al. |
| 5,090,422 A | 2/1992 | Dahl et al. |
| 5,103,837 A | 4/1992 | Weidlich et al. |
| 5,120,813 A | 6/1992 | Ward |
| 5,129,404 A | 7/1992 | Spehr et al. |
| 5,149,739 A | 9/1992 | Lee |
| 5,152,299 A | 10/1992 | Soukup |
| 5,171,760 A | 12/1992 | Kaszas et al. |
| 5,194,505 A | 3/1993 | Brugel |
| 5,212,248 A | 5/1993 | Knoll et al. |
| 5,269,810 A | 12/1993 | Hull et al. |
| 5,282,844 A | 2/1994 | Stokes et al. |
| 5,322,520 A | 6/1994 | Milder |
| 5,324,324 A | 6/1994 | Vachon et al. |
| 5,330,520 A | 7/1994 | Maddison et al. |
| 5,332,791 A | 7/1994 | Knoll et al. |
| 5,332,798 A | 7/1994 | Ferreri et al. |
| 5,340,881 A | 8/1994 | Kennedy et al. |
| 5,385,579 A | 1/1995 | Helland |
| 5,428,123 A | 6/1995 | Ward et al. |
| 5,433,730 A | 7/1995 | Alt |
| 5,442,010 A | 8/1995 | Hauenstein et al. |
| 5,442,015 A | 8/1995 | Kennedy et al. |
| 5,476,496 A | 12/1995 | Strandberg et al. |
| 5,554,178 A | 9/1996 | Dahl et al. |
| 5,589,563 A | 12/1996 | Ward et al. |
| 5,609,622 A | 3/1997 | Soukup et al. |
| 5,630,844 A | 5/1997 | Dogan et al. |
| 5,637,647 A | 6/1997 | Faust |
| 5,663,234 A | 9/1997 | Kennedy et al. |
| 5,665,823 A | 9/1997 | Saxena et al. |
| 5,677,386 A | 10/1997 | Faust |
| 5,681,514 A | 10/1997 | Woody |
| 5,741,331 A | 4/1998 | Pinchuk |
| 5,755,762 A | 5/1998 | Bush |
| 5,766,527 A | 6/1998 | Schildgen et al. |
| 5,837,313 A | 11/1998 | Ding et al. |
| 5,849,415 A | 12/1998 | Shalaby et al. |
| 5,852,118 A | 12/1998 | Horrion et al. |
| 5,853,652 A | 12/1998 | Schildgen et al. |
| 5,861,023 A | 1/1999 | Vachon |
| 5,874,484 A | 2/1999 | Dirckx et al. |
| 5,898,057 A | 4/1999 | Chiang et al. |
| 5,902,329 A | 5/1999 | Hoffmann et al. |
| 5,912,302 A | 6/1999 | Gadkari et al. |
| 5,931,862 A | 8/1999 | Carson |
| 5,987,746 A | 11/1999 | Williams |
| 5,991,667 A | 11/1999 | Feith |
| 6,005,051 A | 12/1999 | Kennedy et al. |
| 6,010,715 A | 1/2000 | Wick et al. |
| 6,072,003 A | 6/2000 | Horrion et al. |
| 6,087,454 A | 7/2000 | Vanhaeren et al. |
| 6,093,197 A | 7/2000 | Bakula et al. |
| 6,117,554 A | 9/2000 | Shalaby et al. |
| 6,200,589 B1 | 3/2001 | Kennedy et al. |
| 6,228,945 B1 | 5/2001 | Kennedy et al. |
| 6,236,893 B1 | 5/2001 | Thong |
| 6,242,058 B1 | 6/2001 | Bahadur et al. |
| 6,253,110 B1 | 6/2001 | Brabec et al. |
| 6,256,541 B1 | 7/2001 | Heil et al. |
| 6,284,682 B1 | 9/2001 | Troczynski et al. |
| 6,361,780 B1 | 3/2002 | Ley et al. |
| 6,363,286 B1 | 3/2002 | Zhu et al. |
| 6,365,674 B1 | 4/2002 | Kaufhold et al. |
| 6,426,114 B1 | 7/2002 | Troczynski et al. |
| 6,444,334 B1 | 9/2002 | Doi et al. |
| 6,545,097 B2 | 4/2003 | Pinchuk et al. |
| 6,555,619 B1 | 4/2003 | Kennedy et al. |
| 6,600,956 B2 | 7/2003 | Maschino et al. |
| 6,627,724 B2 | 9/2003 | Meijs et al. |
| 6,709,514 B1 | 3/2004 | Hossainy |
| 6,730,324 B2 | 5/2004 | Troczynski et al. |
| 6,770,325 B2 | 8/2004 | Troczynski et al. |
| 6,808,766 B1 | 10/2004 | Miyama et al. |
| 6,827,881 B2 | 12/2004 | Molnar et al. |
| 6,849,667 B2 | 2/2005 | Haseyama et al. |
| 6,870,024 B2 | 3/2005 | Haubennestel et al. |
| 6,889,092 B2 | 5/2005 | Zhu et al. |
| 6,896,965 B1 | 5/2005 | Hossainy |
| 7,013,182 B1 | 3/2006 | Krishnan |
| 7,065,411 B2 | 6/2006 | Verness |
| 7,101,956 B2 | 9/2006 | Benz et al. |
| 7,105,622 B2 | 9/2006 | Kennedy et al. |
| 7,115,300 B1 | 10/2006 | Hossainy |
| 7,119,138 B1 | 10/2006 | Feeney et al. |
| 7,174,221 B1 | 2/2007 | Chen et al. |
| 7,196,142 B2 | 3/2007 | Kennedy et al. |
| 7,231,259 B2 | 6/2007 | Jenney et al. |
| 7,247,364 B2 | 7/2007 | Hossainy et al. |
| 7,279,175 B2 | 10/2007 | Chen et al. |
| 7,280,875 B1 | 10/2007 | Chitre et al. |
| 7,289,856 B1 | 10/2007 | Karicherla |
| 7,292,890 B2 | 11/2007 | Whitehurst et al. |

(56) References Cited

U.S. PATENT DOCUMENTS

| | | | |
|---|---|---|---|
| 7,347,751 B2 | 3/2008 | Sweeney et al. | |
| 7,358,306 B2 | 4/2008 | Turri et al. | |
| D579,758 S | 11/2008 | Tanaka et al. | |
| 7,504,052 B2 | 3/2009 | Ehbing et al. | |
| 7,553,546 B1 | 6/2009 | Tan | |
| 7,617,004 B2 | 11/2009 | Bartels et al. | |
| 7,715,922 B1 | 5/2010 | Tan | |
| 7,756,589 B2 | 7/2010 | Krishnan | |
| 7,881,808 B2 | 2/2011 | Borgaonkar et al. | |
| 7,979,142 B2 | 7/2011 | Krishnan | |
| 8,163,826 B2 | 4/2012 | Willberg et al. | |
| 8,324,290 B2 | 12/2012 | Desai et al. | |
| 8,349,123 B2 | 1/2013 | Zhang et al. | |
| 8,372,468 B2 | 2/2013 | Desai et al. | |
| 8,374,704 B2 | 2/2013 | Desai et al. | |
| 8,501,831 B2 | 8/2013 | Desai et al. | |
| D689,734 S | 9/2013 | Bock | |
| 8,529,934 B2 | 9/2013 | Desai et al. | |
| 8,644,952 B2 | 2/2014 | Desai et al. | |
| 8,660,663 B2 | 2/2014 | Wolf et al. | |
| 8,674,034 B2 * | 3/2014 | Kennedy | C08G 18/10 525/460 |
| 8,676,344 B2 | 3/2014 | Desai et al. | |
| 8,889,926 B2 | 11/2014 | Kennedy et al. | |
| 8,903,507 B2 | 12/2014 | Desai et al. | |
| 8,927,660 B2 * | 1/2015 | Desai | A61L 27/16 525/455 |
| 8,962,785 B2 | 2/2015 | Faust et al. | |
| 9,574,043 B2 | 2/2017 | Faust et al. | |
| 9,655,720 B2 | 5/2017 | Bluestein et al. | |
| 9,926,399 B2 | 3/2018 | Faust et al. | |
| 2002/0012694 A1 | 1/2002 | Moo-Young et al. | |
| 2002/0022826 A1 | 2/2002 | Reynolds et al. | |
| 2002/0138123 A1 | 9/2002 | Casas-Bejar et al. | |
| 2003/0031699 A1 | 2/2003 | Van Antwerp | |
| 2003/0073961 A1 | 4/2003 | Happ | |
| 2003/0093136 A1 | 5/2003 | Osypka et al. | |
| 2003/0125499 A1 | 7/2003 | Benz et al. | |
| 2003/0204022 A1 | 10/2003 | Kennedy et al. | |
| 2004/0037886 A1 | 2/2004 | Hsu | |
| 2004/0054210 A1 | 3/2004 | Benz et al. | |
| 2004/0059402 A1 | 3/2004 | Soukup et al. | |
| 2004/0063805 A1 | 4/2004 | Pacetti et al. | |
| 2004/0068036 A1 | 4/2004 | Halladay et al. | |
| 2004/0143255 A1 | 7/2004 | Vanney et al. | |
| 2004/0175558 A1 | 9/2004 | Fozan El-Nounou et al. | |
| 2004/0186545 A1 | 9/2004 | Rosero et al. | |
| 2004/0193139 A1 | 9/2004 | Armstrong et al. | |
| 2004/0198901 A1 | 10/2004 | Graham et al. | |
| 2005/0031874 A1 | 2/2005 | Michal et al. | |
| 2005/0037050 A1 | 2/2005 | Weber | |
| 2005/0060022 A1 | 3/2005 | Felt et al. | |
| 2005/0070985 A1 | 3/2005 | Knapp et al. | |
| 2005/0079199 A1 | 4/2005 | Heruth et al. | |
| 2005/0080470 A1 | 4/2005 | Westlund et al. | |
| 2005/0180919 A1 | 8/2005 | Tedeschi | |
| 2005/0288476 A1 | 12/2005 | Yilgor et al. | |
| 2006/0047083 A1 | 3/2006 | Yilgor et al. | |
| 2006/0047098 A1 | 3/2006 | Anna et al. | |
| 2006/0135721 A1 | 6/2006 | Lange | |
| 2006/0142503 A1 | 6/2006 | Lang et al. | |
| 2006/0223946 A1 | 10/2006 | Faust et al. | |
| 2006/0235499 A1 | 10/2006 | Heil, Jr. et al. | |
| 2006/0264577 A1 | 11/2006 | Faust et al. | |
| 2007/0051531 A1 | 3/2007 | Borgaonkar et al. | |
| 2007/0093604 A1 | 4/2007 | Kennedy et al. | |
| 2007/0106144 A1 | 5/2007 | Squeri | |
| 2007/0128246 A1 | 6/2007 | Hossainy et al. | |
| 2007/0151531 A1 | 7/2007 | Masaoka et al. | |
| 2007/0190104 A1 | 8/2007 | Kamath et al. | |
| 2007/0190108 A1 | 8/2007 | Datta et al. | |
| 2007/0190319 A1 | 8/2007 | Kalayci | |
| 2007/0203302 A1 | 8/2007 | Kennedy et al. | |
| 2007/0282411 A1 | 12/2007 | Franz et al. | |
| 2008/0008739 A1 | 1/2008 | Hossainy et al. | |
| 2008/0009939 A1 | 1/2008 | Gueriguian et al. | |
| 2008/0051866 A1 | 2/2008 | Chen et al. | |
| 2008/0095918 A1 | 4/2008 | Kleiner et al. | |
| 2008/0167423 A1 | 7/2008 | Richards et al. | |
| 2008/0167710 A1 | 7/2008 | Dave et al. | |
| 2008/0311173 A1 | 12/2008 | Schwarz et al. | |
| 2009/0054961 A1 | 2/2009 | Borgaonkar et al. | |
| 2009/0187162 A1 | 7/2009 | Ohara et al. | |
| 2009/0292094 A1 | 11/2009 | Larichev et al. | |
| 2009/0326077 A1 | 12/2009 | Desai et al. | |
| 2010/0023104 A1 | 1/2010 | Desai et al. | |
| 2010/0025703 A1 | 2/2010 | Towns et al. | |
| 2010/0055470 A1 | 3/2010 | Klun et al. | |
| 2010/0069578 A1 | 3/2010 | Faust et al. | |
| 2010/0075018 A1 | 3/2010 | Desai et al. | |
| 2010/0107967 A1 | 5/2010 | Tanaka et al. | |
| 2010/0179298 A1 | 7/2010 | Faust et al. | |
| 2010/0241204 A1 | 9/2010 | Scheuermann | |
| 2010/0241208 A1 | 9/2010 | Pinchuk | |
| 2010/0241209 A1 | 9/2010 | Krishnan | |
| 2010/0249296 A1 | 9/2010 | Kimura et al. | |
| 2010/0267897 A1 | 10/2010 | Kennedy et al. | |
| 2011/0045030 A1 | 2/2011 | Desai et al. | |
| 2011/0051581 A1 | 3/2011 | Janik et al. | |
| 2011/0054580 A1 | 3/2011 | Desai et al. | |
| 2011/0054581 A1 | 3/2011 | Desai et al. | |
| 2011/0087317 A1 | 4/2011 | Borgaonkar et al. | |
| 2011/0152989 A1 | 6/2011 | Tan | |
| 2011/0213084 A1 | 9/2011 | Kennedy et al. | |
| 2012/0077934 A1 | 3/2012 | Faust et al. | |
| 2012/0158107 A1 | 6/2012 | Wolf et al. | |
| 2012/0259069 A1 | 10/2012 | Kennedy et al. | |
| 2012/0309661 A1 | 12/2012 | Adams et al. | |
| 2013/0013040 A1 | 1/2013 | Desai et al. | |
| 2013/0041108 A1 | 2/2013 | Kennedy et al. | |
| 2013/0041442 A1 | 2/2013 | Arnholt et al. | |
| 2013/0079487 A1 | 3/2013 | Faust et al. | |
| 2013/0122185 A1 | 5/2013 | Desai et al. | |
| 2013/0131765 A1 | 5/2013 | Polkinghorne et al. | |
| 2013/0330390 A1 | 12/2013 | Pacetti | |
| 2013/0331538 A1 | 12/2013 | Kennedy et al. | |
| 2014/0074201 A1 | 3/2014 | Arnholt et al. | |
| 2014/0088218 A1 | 3/2014 | Desai et al. | |
| 2014/0144580 A1 | 5/2014 | Desai et al. | |
| 2014/0194963 A1 | 7/2014 | Desai et al. | |
| 2015/0274876 A1 | 10/2015 | Faust | |
| 2016/0008607 A1 | 1/2016 | Kane et al. | |
| 2016/0024340 A1 | 1/2016 | Rukavina | |
| 2016/0145362 A1 | 5/2016 | Wettling et al. | |
| 2016/0311983 A1 | 10/2016 | Delaney et al. | |
| 2017/0137558 A1 | 5/2017 | Faust et al. | |
| 2017/0174845 A1 | 6/2017 | Delaney, Jr. et al. | |
| 2017/0327622 A1 | 11/2017 | Delaney et al. | |
| 2018/0208698 A1 | 7/2018 | Faust et al. | |
| 2018/0258196 A1 | 9/2018 | Delaney, Jr. et al. | |

FOREIGN PATENT DOCUMENTS

| | | |
|---|---|---|
| CN | 1221430 A | 6/1999 |
| CN | 1248606 A | 4/2006 |
| CN | 102131530 A | 7/2011 |
| CN | 102365308 A | 2/2012 |
| CN | 102712808 A | 10/2012 |
| CN | 104231207 A | 12/2014 |
| CN | 104520345 A | 4/2015 |
| CN | ZL2010800475975 B | 4/2015 |
| CN | 104592850 A | 5/2015 |
| CN | 104602888 A | 5/2015 |
| CN | 104610902 A | 5/2015 |
| DE | 19610350 A1 | 9/1997 |
| EP | 0153520 A1 | 9/1985 |
| EP | 0259492 A1 | 3/1988 |
| EP | 0610714 A2 | 8/1994 |
| EP | 0732349 A2 | 9/1996 |
| EP | 0837097 A1 | 4/1998 |
| EP | 1061092 A1 | 12/2000 |
| EP | 1489109 A2 | 12/2004 |
| EP | 2006328 A1 | 12/2008 |
| EP | 2922888 A2 | 9/2015 |

(56) References Cited

FOREIGN PATENT DOCUMENTS

| | | |
|---|---|---|
| JP | 02088614 A | 3/1990 |
| JP | 4154815 A | 5/1992 |
| JP | 6345821 A | 12/1994 |
| JP | 7102017 A | 4/1995 |
| JP | 7330591 A | 12/1995 |
| JP | 07331223 A | 12/1995 |
| JP | 1087726 A | 4/1998 |
| JP | 11131325 A | 5/1999 |
| JP | 2000169814 A | 6/2000 |
| JP | 2001011319 A | 1/2001 |
| JP | 2001040064 A | 2/2001 |
| JP | 2001131879 A | 5/2001 |
| JP | 2002348317 A | 12/2002 |
| JP | 2003137951 A | 5/2003 |
| JP | 2004204181 A | 7/2004 |
| JP | 2006515795 A | 6/2006 |
| JP | 2008238761 A | 10/2008 |
| JP | 2009132832 A | 6/2009 |
| JP | 2009535182 A | 10/2009 |
| JP | 2009540873 A | 11/2009 |
| JP | 2011526326 A | 10/2011 |
| JP | 2012515231 A | 7/2012 |
| JP | 2012519053 A | 8/2012 |
| JP | 2013502495 A | 1/2013 |
| JP | 2014533580 A | 12/2014 |
| JP | 2015523192 A | 8/2015 |
| WO | WO1987004625 A1 | 8/1987 |
| WO | WO9316131 A1 | 8/1993 |
| WO | WO1993022360 A1 | 11/1993 |
| WO | WO1995026993 A1 | 10/1995 |
| WO | WO1997000293 A1 | 1/1997 |
| WO | WO9707161 A1 | 2/1997 |
| WO | WO1997047664 A1 | 12/1997 |
| WO | WO1998033832 A1 | 8/1998 |
| WO | WO1998034678 A1 | 8/1998 |
| WO | 1999051656 A1 | 10/1999 |
| WO | WO200213785 A2 | 2/2002 |
| WO | WO2003042273 A1 | 5/2003 |
| WO | WO2004014453 A1 | 2/2004 |
| WO | WO2004044012 A1 | 5/2004 |
| WO | WO2004113400 A2 | 12/2004 |
| WO | WO2005035655 A1 | 4/2005 |
| WO | WO2006011647 A1 | 10/2006 |
| WO | WO2006110647 A1 | 10/2006 |
| WO | WO2007030722 A1 | 3/2007 |
| WO | WO2007117566 A2 | 10/2007 |
| WO | WO2007119687 A1 | 10/2007 |
| WO | 2007130900 A2 | 11/2007 |
| WO | WO2007126806 A1 | 11/2007 |
| WO | WO2008060333 A1 | 5/2008 |
| WO | WO2008066914 A1 | 6/2008 |
| WO | WO2008112190 A1 | 9/2008 |
| WO | WO2008127730 A1 | 10/2008 |
| WO | WO2008156806 A1 | 12/2008 |
| WO | WO2009051945 A1 | 4/2009 |
| WO | WO2009058397 A1 | 5/2009 |
| WO | WO2009158600 A1 | 12/2009 |
| WO | WO2009158609 A1 | 12/2009 |
| WO | WO2010039986 A1 | 4/2010 |
| WO | WO2010078552 A1 | 7/2010 |
| WO | WO2010081132 A1 | 7/2010 |
| WO | 2010107530 A2 | 9/2010 |
| WO | WO2010111280 A1 | 9/2010 |
| WO | 2010135418 A2 | 11/2010 |
| WO | WO2011022583 A1 | 2/2011 |
| WO | WO2011060161 A1 | 5/2011 |
| WO | 2012093597 A1 | 7/2012 |
| WO | WO2013192186 A1 | 12/2013 |
| WO | 2014018509 A1 | 1/2014 |
| WO | 2014081916 A2 | 5/2014 |
| WO | WO2015007553 A1 | 1/2015 |
| WO | 2016007367 A1 | 1/2016 |
| WO | 2017106774 A1 | 6/2017 |
| WO | 2017127642 A1 | 7/2017 |

OTHER PUBLICATIONS

Non-Final Office Action issued in U.S. Appl. No. 11/400,059, dated Apr. 11, 2011.
Non-Final Office Action issued in U.S. Appl. No. 12/492,483, dated Nov. 21, 2011, 11 pages.
Non-Final Office Action, issued in U.S. Appl. No. 12/685,858, dated Feb. 15, 2012, 18 pages.
Notice of Allowance issued in U.S. Appl. No. 12/492,483, dated Jul. 13, 2012, 9 pages.
Notification of Transmittal of the International Search Report and the Written Opinion of the International Searching Authority for Int'l Application No. PCT/US2013/071170, entitled: High Strength Polyisobutylene Polyurethanes, dated Jun. 6, 2014.
Odian, G. "Principles of Polymerization," Wiley Interscience (2004), pp. 80-83.
Office Action issued in EP 07754128 dated Mar. 31, 2010.
Office Action issued in EP Application No. 07754128.2, dated Feb. 19, 2009, 3 pages.
Office Action issued in U.S. Appl. No. 11/400,059, dated Aug. 24, 2010.
Ojha et al., "Synthesis and Characterization of Thermoplastic Polyurethaneureas based on Polyisobutylene and Poly (tetramethylene oxide) Segments", J. Macromolecular Science, Part A, vol. 47(3), pp. 186-191, Mar. 2010.
Ojha, Umaprasana et al., "Syntheses and characterization of novel biostable polyisobutylene based thermoplastic polyurethanes", Polymer 50(2009), 3448-3457.
Ojha, Umaprasana et al., "Synthesis and Characterization of Endfunctionalized Polyisobutylenes for Sharpless-type Click Reactions", Polymer Preprints 2007, 48(2), 786.
Ojha, Umaprasana, et al. Syntheses and Characterization of Novel Biostable Polyisobutylene Based Thermoplastic Polyurethanes. Polymer 50:3448-3457, 2009.
Pinchuk, L. Review: A Review of the Biostability and Carcinogenicity of Polyurethanes in Medicine and the New Generation of 'Biostable' Polyurethanes. J. Biomater. Sci., Polymer Edn., 6(3):225-267, 1994.
Prucker, O., et al. Photochemical Attachment of Polymer Films to Solid Surfaces via Monolayers of Benzophenone Derivatives. J. Am. Chem. Soc. 121:8766-8770, 1999.
Puskas, J.E. et al., "polyisobutylene-based biomaterials", Journal of Polymer Science Part A: Polymer Chemistry, vol. 42, Issue 13 (2004) pp. 3091-3109.
Rajkhowa, Ritimoni et al., "Efficient syntheses of hydroxyallyl end functional polyisobutylenes, a precursors to thermoplastic polyurethanes", Polymer Reprints (American Chemical Society, Division of Polymer Chemistry) 2007, 48 (2), 233-234.
Ranade, S. et al., "Physical characterization of controlled release of paclitaxel from the TAXUS™ Express2™ drug-eluting stent", Journal of Biomedical Materials Research Part A, 71A (2004) 625-634.
Ranade, S.V. et al., Styrenic Block copolymers for Biomaterial and Drug Delivery Applications, Acta Biomater. Jan. 2005; 1(1): 137-44.
Response filed Aug. 31, 2009 to Office Action dated Feb. 19, 2009, EP App 07754128.
Saiani, A., et. al. Origin of Multiple Melting Endotherms in a High Hard Block Content Polyurethane. 1. Thermodynamic Investigation. Macromolecules, 34:9059-9068, 2001.
Saiani, A., et. al. Origin of Multiple Melting Endotherms in a High Hard Block ContentPolyurethane. 2. Structural Investigation. Macromolecules, 37:1411-1421, 2004.
Santos, R. et al., "New Telechelic Polymers and Sequential Copolymers by Polyfunctional Initiator-Transfer-Agents (Inifers)", Polymer Bulletin, 11:341-348 (1984).
Schellekens, Yves, et al. "Tin-Free Catalysts for Production of Aliphatic Thermoplastic Polyurethanes." Green Chemistry, 16:4401-4407, 2014.
Second Office Action for Chinese Application No. 201380042582.3 entitled "High Strength Polyisobutylene Polyurethanes" dated May 10, 2016 consisting of 5 pages.

(56) References Cited

OTHER PUBLICATIONS

Siefken, Von Werner. "Mono- and Polyisocyanate, IV. Mitteilung uber Polyurethane," [With machine English translation]. Justus Liebigs Annalen Der Chemie, 562(2):75-136, 1949.
Simmons, Anne. et al., "The effect of sterilisation on a poly(dimethylsiloxane)/poly(hexamethylene oxide) mixed macrodiol-based Polyurethane elastomer", Biomaterials 2006, 27, 4484-4497.
Singh, Vishwakarma; et al. "Molecular complexity from aromatics. Cycloaddition of spiroepoxycyclohexa-2,4-dienones and intramolecular Diels-Alder reaction: a stereoselective entry into tetracyclic core of atisane diterpenoids." Tetrahedron 69 (2013) 137-146.
Six, Christian, et al. "Isocyanates, Organic." Ullmann's Encyclopedia of Industrial Chemistry, vol. 20:63-82, 2012.
Speckhard, T. A., et. al. Properties of Polyisobutylene Polyurethane Block Copolymers: 2. Macroglycols Produced by the "Inifer" Technique. Polymer, 26:55-69, 1985.
Speckhard, T.A. et al., "New generation polyurethanes", Polymer News 1984, 9(12), 354-358.
Speckhard, T.A. et al., "Properties of Polyisobutylene Polyurethane Block Copolymers: 2. Macroglycols produced by the 'inifer' technique", Polymer, vol. 26, No. 1, Jan. 1985, pp. 55-78.
Speckhard, T.A. et al., "Properties of Polyisobutylene Polyurethane Block Copolymers: 3. hard segments based on 4,4'-dicyclohexylmethane diisocyanate (H12MDI) and butane diol", Polymer, vol. 26, No. 1, Jan. 1985, pp. 70-78.
Speckhard, T.A. et al., "Properties of Polyisobutylene-Polyurethane Block Copolymers", Journal of Elastomers and Plastics, vol. 15 (Jul. 1983), pp. 183-192.
Speckhard, T.A. et al., "Properties of Polyisobutylene-Polyurethane Block Copolymers: I. Macroglycols from Ozonolysis of Isobutylene-Isoprene Copolymer", Polymer Engineering and Science, Apr. 1983, vol. 23. No. 6, pp. 337-349.
Speckhard, T.A. et al., "Ultimate Tensite Properties of Segmented Polyurethane Elastomers", Rubber Chem. Technol., 59, 405-431 (1986).
Stokes, K., et. al. Polyurethane Elastomer Biostability. Journal of Biomaterials Applications, 9:321-354, 1995.
Storey, Robson F.; et al. "Carbocation Rearrangement in Controlled/Living Isobutylene Polymerization," Macromolecules 1998, 31, pp. 1058-1063.
Tan, J. et al., "In Vivo Biostability Study of a New Lead Insulation Material," Cardiostim 2006, Europace Supplements, 8, 179PW/9 (2006).
Third Office Action for Chinese Application No. 201380042582.3, entitled "High Strength Polyisobutylene Polyurethanes" dated Jul. 27, 2016 consisting of 5 pages.
Tonelli, C. et al., "New Fluoro-Modified Thermoplastic Polyurethanes" Journal of Applied Polymer Science, vol. 87, Issue 14 (2003) 2279-2294.
Tonelli, Claudio et al., "New Perfluoropolyether Soft Segment Containing Polyurethanes", Journal of Applied Polymer Science vol. 57, pp. 1031-1042 (1995).
Virmani, R. et al. Circulation Feb. 17, 2004, 109)6) 701-5.
Viski, Peter, et al. "A Novel Procedure for the Cleavage of Olefin Derivatives to Aldehydes Using Potassium Permanganate." J. Org. Chem., 51:3213-3214, 1986.
Wang, F. Polydimethylsiloxane Modification of Segmented Thermoplastic Polyurethanes and Polyureas, PhD. Dissertation, Virginia Polytechnic Institute and State university, Apr. 13, 1998.
Weisberg, David M. et al., "Synthesis and Characterization of Amphiphilic Poly(urethaneurea)-comb-polyisobutylene Copolymers", Macromolecules 2000, 33(12), pp. 4380-4389.
Weiss, H. G.; et al. "Diborane from the Sodium Borohydride-Sulfuric Acid Reaction." Contribution From Research Laboratory, Olin Mathieson Chemical Corporation, Dec. 5, 1959, 81(23):6167-6168.
Weissmuller, M. et al., "Preparation and end-linking of hydroxyl-terminated polystyrene star macromolecules", Macromolecular Chemistry and Physics 200(3), 1999, 541-551.

Wiggins, Michael J. et al., "Effect of soft-segment chemistry on polyurethane biostability during in vitro fatigue loading", Journal of biomedical materials research, 68(4), 2004, 668-683.
International Preliminary Report on Patentability issued in PCT/US2017/031856, 7 pages.
International Search Report and Written Opinion issued in PCT/US2018/046813, dated Dec. 11, 2018, 11 pages.
International Search Report and Written Opinion issued in PCT/US2011/061692, dated Feb. 9, 2012, 9 pages.
International Search Report and Written Opinion issued in PCT/US2013/053448, dated Apr. 28, 2014, 11 pgs.
International Search Report and Written Opinion issued in PCT/US2013/053448, dated Jul. 28, 2014, correcting earlier version dated Apr. 28, 2014, 11 pages.
International Search Report and Written Opinion issued in PCT/US2016/027294 dated Jul. 28, 2016, 10 pages.
International Search Report and Written Opinion issued in PCT/US2016/067363, dated Mar. 3, 2017, 10 pages.
International Search Report and Written Opinion issued in PCT/US2017/031856, dated Aug. 11, 2017, 9 pages.
International Search Report and Written Opinion issued in PCT/US2018/021311, dated May 24, 2018, 11 pages.
International Search Report issued in PCT/US2009/048827, dated Oct. 6, 2009, 3 pages.
International Search Report issued in PCT/US2009/048845, dated Oct. 6, 2009, 3 pages.
International Search Report issued in PCT/US2010/020733, dated May 6, 2010.
Ioffe, David et al., "Bromine, Organic Compounds", Kirk-Othmer Encyclopedia of Chemical Technology, vol. 4, pp. 340-365, © 2002.
Ivan, B. et al., "Synthesis of New Polyisobutylene-Based Polyurethanes", Am. Chem. Soc., Div. Org. Coat. Plast. Prepr., 43, 908-913 (1980).
Ivan, B., et. al. Living Carbocationic Polymerization. XXX. One-Pot Synthesis of Allyl-Terminated Linear and Tri-Arm Star Polyisobutylenes, and Epoxy- and Polyisobutylenes, and Epoxy- and Hydroxy-Telechelics Therefrom. Journal of Polymer Science: Part A: Polymer Chemistry, 28:89-104, 1990.
Ivan, Bela, et. al. New Telechelic Polymers and Sequential Copolymers by Polyfunctional Initiator-Transfer Agents (Inifers). VII. Synthesis and Characterization of alpha,omega-Di(hydroxy) Polyisobutylene. Journal of Polymer Science: Polymer Chemistry Edition, 18:3177-3191, 1980.
Ivan, Bela; et al. "Living Carbocationic Polymerization. XXX. One-Pot Synthesis of Allyl-Terminated Linear and Tri-Arm Star Polyisobutylenes, and Epoxy- and Hydroxy-Telechelics Therefrom." Journal of Polymer Science: Part A: Polymer Chemistry, vol. 28, 89-104 (1990).
Jenny, C. et al., "A New Insulation Material for Cardiac Leads with Potential for Improved performance", HRS 2005, HeartRhythm, 2, S318-S319 (2005).
Jewrajka, Suresh K. et al., "Polyisobutylene-Based Polyurethanes. II. Polyureas Containing Mixed PIB/PTMO Soft Segments", Journal of Polymer Science: Part A: Polymer Chemistry, vol. 47, 2787-2797 (2009).
Jewrajka, Suresh K. et al., "Polyisobutylene-Based Segmented Polyureas. I. Synthesis of Hydrolytically and Oxidatively Stable Polyureas", Journal of Polymer Science: Part A: Polymer Chemistry, vol. 47, 38-48 (2009).
Kabalka, George W.; et al. "N-t-Butoxycarbonyl Protection of Primary and Secondary Amines in the Hydroboration Reaction: Synthesis of Amino Alcohols." Synthetic Communications: An International Journal for Rapid Communication of Synthetic Organic Chemistry, 25(14), 2135-2143 (1995).
Kali, Gergely; et al. "Anionic Amphiphilic End-Linked Conetworks by the Combination of Quasiliving Carbocationic and Group Transfer Polymerizations." Journal of Polymer Science, Part A—Polymer Chemistry, 2009, 47(17):4289-4301.
Kang, Jungmee et al, "PIB-Based Polyurethanes. IV. The Morphology of Polyurethanes Containing Soft Co-Segments", Journal of Polymer Science Part A: Polymer Chemistry, vol. 47, 6180-6190 (2009).

(56) References Cited

OTHER PUBLICATIONS

Kang, Jungmee et al., "Rendering Polyureas Melt Processible", Journal of Polymer Science Part A: Polymer Chemistry, vol. 49, 2461-2467 (2011).
Kang, Jungmee et al., Polyisobutylene-Based Polyurethanes. V. Oxidative-Hydrolytic Stability and Biocampatibility, Journal of Polymer Science: Part A: Polymer Chemistry, vol. 48, 2194-2203 (2010).
Kang, Jungmee, et al. Polyisobutylene-Based Polyurethanes with Unprecedented Properties and How They Came About. Polymer Chemistry, 49:3891-3904.
Kennedy, J.P. et al., "Designed Polymers by Carbocationic Macromolecular Engineering: Theory and practice", Hanser Publishers 1991, pp. 191-193 and 226-233.
Kennedy, J.P. et al., "Polyisobutylene-Based Diols and Polyurethanes", Urethane Chemistry and Applications, Ed., K. H. Edwards, ACS Symp. Book Series, 172, Washington, D.C. 1981, pp. 383-391.
Kennedy, J.P. et al., "Polyisobutylene-Based Diols and Polyurethanes" Advances in Urethane Science and Technology, vol. 8, 1981, pp. 245-251.
Kennedy, J.P. et al., "Polyisobutylene-based Model urethane Networks, I. Initial characterization and Physical properties", Polymeric Materials Science and Engineering, vol. 49, Copyright 1983 by ACS, pp. 69-77.
Kennedy, Joseph P. Synthesis, Characterization and Properties of Novel Polyisobutylene-Based urethane Model Networks, Journal of Applied Polymer Science, vol. 33(7), May 20, 1987, pp. 2449-2465.
Kennedy, Joseph P. "Synthesis, Characterization and Properties of Polyisobutylene-Based Polyurethanes", 6th International Technical/Marketing Conference: Polyurethane—New Paths to Progress-Marketing—Technology, Journal of Cellular Plastics, 1983, 19:288-307.
Kennedy, Joseph P. "Synthesis, Characterization and Properties of Polyisobutylene-Based Polyurethanes", Journal of Elastomers and Plastics, vol. 17 (Jan. 1985), pp. 82-88
Kennedy, Joseph P. "Synthesis, Characterization and Properties of Polyisobutylene-Based Polyurethanes", The Society of the Plastics Industry, Inc., polyurethane Division, Proceedings of the SPI—6th International Technical/Marketing Conference, Nov. 2-4, 1983, San Diego, CA, pp. 514-516.
Kennedy, Joseph P., "Polyurethanes Based on Polyisobutylenes", Chemtech, Nov. 1986, 16(11), pp. 694-697.
Kirby, Darren, "Use of a Bioactive Material on a Pacemaker Electrode for the Purpose of Enhancing Heart Pace/Sense Efficiency", MSC Biomedical Engineering, Thesis, Trinity College Dublin (2003).
Koberstein, J. T., et. al. Compression-Molded Polyurethane Block Copolymers. 1. Microdomain Morphology and Thermomechanical Properties. Macromolecules, 25:6195-6204, 1992.
Koberstein, J. T., et. al. Compression-Molded Polyurethane Block Copolymers. 2. Evaluation of Microphase Compositions. Macromolecules, 25:6205-6213, 1992.
Koberstein, J. T., et. al. Simultaneous SAXS-DSC Study of Multiple Endothermic Behavior in Polyether-Based Polyurethane Block Copolymers. Macromolecules, 19:714-720, 1986.
Kunal, K., et. al. Polyisobutylene: A Most Unusual Polymer. Journal of Polymer Science: Part B: Polymer Physics, 46:1390-1399, 2008.
Lazzarato, Loretta; et al. "(Nitrooxyacyloxy)methyl Esters of Aspirin as Novel Nitric Oxide Releasing Aspirins." J. Med. Chem. 2009, 52, 5058-5068.
Lelah, M.D. et al., "Polyurethanes in Medicine", CRC Press, Boca Raton, FL 1986, Chapter 3.
Leung, L. M., et. al. DSC Annealing Study of Microphase Separation and Multiple Endothermic Behavior in Polyether-Based Polyurethane Block Copolymers. Macromolecules, 19:706-713, 1986.
Li, J. et al., "Polyisobutylene supports—a non-polar hydrocarbon analog of PEG supports", Tetrahedron, 61 (51):12081-12092, Dec. 2005.

Macias, A. et al., "Preparacion y reticulacion de poliisobutilenos de bajo peso molecular con grupos terminales reactivos", Revista de Plasticos Modernos, Num 332 (Apr. 1983), pp. 412-418.
Martin, D. J., et. al. Polydimethylsiloxane/Polyether-Mixed Macrodiol-Based Polyurethane Elastomers: Biostability. Biomaterials, 21:1021-1029, 2000.
Miller, J. A., "New Directions in Polyurethane Research", Organic Coatings and Applied Polymer Science Proceedings, vol. 47, Copyright 1982 by ACS, pp. 124-129.
Mitzner, E. et al., "Modification of poly(ether urethane) elastomers by incorporation of poly(isobutylene) glycol. Relation between polymer properties and thrombogenicity", J. Biomater. Sci. Polymer edn. vol. 7, No. 12, pp. 1105-1118 (1996).
Mitzner, E., "Modification of segmented poly(ether urethanes) by incorporation of Poly(isobutylene)glycol", J.M.S.—Pure Appl. Chem., A34(1), pp. 165-178 (1997).
Mitzner, E., et. al. Modification of Segmented Poly(Ether Urethanes) by Incorporation of Poly(Isobutylene)Glycol. Journal of Macromolecular Science, Part A., Pure and Applied Chemistry, 34(1):165-178, 1997.
Miyabayashi, Toshio et al., "Characterization of Polyisobutylene-Based Model Urethane Networks", Journal of Applied Polymer Science, vol. 31, pp. 2523-2532 (1986)
Motte, S., & Kaufman, L. J. (2012). Strain stiffening in collagen I Networks. Biopolymers, 99(1):35-46.
Wohlfarth, C., "Permittivity (Dielectric Constant) of Liquids", CRC Handbook, 91st ed. 2010-2011, p. 6-186 to 6-207.
Wright, James I., "Using Polyurethanes in Medical Applications", 5 pages. Downloaded from http://www.cmdm.com on Oct. 17, 2006.
Wu, Yuguang et al., "The role of adsorbed fibrinogen in platelet adhesion to polyurethane surfaces: A comparison of surface hydrophobicity, protein adsorption, monoclonal antibody binding, and platelet adhesion", Journal of Biomedical Materials Research, Part A, Sep. 15, 2005, vol. 74A, No. 4, pp. 722-738.
Xu, Ruijian et al., "Low permeability biomedical polyurethane nanocomposites", Journal of Miomedical Materials Resarch, 2003, vol. 64A, pp. 114-119.
Yang, M. et al., J. biomed. Mater. Res. 48 (1999) 13-23.
Yeh, J. et al., "Moisture diffusivity of Biomer® versus Biomer®-coated Polyisobutylene polyurethane urea (PIB-PUU): a potential blood sac material for the artificial heart", Journal of Materials Science Letters 13(19), 1994, pp. 1390-1391.
Yoon, Sung C. et al., "Surface and bulk structure of segmented poly(ether urethanes) with Perfluoro Chain Extenders. 5. Incorporation of Poly(dimethylsiloxane) and Polyisobutylene Macroglycols", Macromolecules Mar. 14, 1994, 27(6), pp. 1548-1554.
York, P., "New Materials and Systems for Drug Delivery and Targeting", Chemical Aspects of Drug Delivery Systems, Copyright 1996, pp. 1-10, proceedings from a symposium held Apr. 17-18, 1996 at Salford University.
Zhang, F., et. al. Glassy Carbon as an Absolute Intensity Calibration Standard for Small-Angle Scattering. Metallurgical and Materials Transactions A, 41A:1151-1158, May 2010.
"Butyl Rubber Properties and Applications", downloaded form URL: hiit://ww.iisrp.com/WebPolymers/02ButylRubberllR.pdf. availale on the internet on Jul. 31, 2007 according to Wayback Web Archive.
Ako, Masayuke et al., "Polyisobutylene-based urethane foams I. Comparative reactivities of hydroxyl-terminated polyisobutylenediols and -triols and other hydroxyl-capped polyols with isocyanate", Polymer Bulletin 19(2), 137-143 (1988).
Ako, Masayuke et al., "Polyisobutylene-based urethane foams II. Synthesis and properties of novel polyisobutylene-based flexible polyurethane foams", Journal of Applied Polymer Science, vol. 37(5), Feb. 5, 1989, pp. 1351-1361.
Bacaloglu, R. and Cotarca, L. "Reactions of Aryl Isocyanates with Alcohols in the Presence Ob Tertiary Amines." Journal f. prakt. Chemie. , 330(4):530-540.
Bela et al., Living Carbocation Polymerization. XX. Synthesis of Allyl-Telechelic Polyisobutylenes by One-Pot Polymerization-Functionalization polymer. Mater. Sci. Eng. 1988; 58:869-872.
Chang, Victor S.C. et al. "Gas Permeability, Water Absorption, Hydrolytic Stability and Air-Oven Aging of Polyisobutylene-Based Polyurethane Networks", Polymer Bulletin 8(2-3-4), 69-74 (1982).

(56) References Cited

OTHER PUBLICATIONS

Chen, Chi-Chang et al., "Solid Polymer Electrolytes III Preparation, Characterization, and Ionic Conductivity of New Gelled Polymer Electrolytes Based on Segmented, Perfluoropolyether-Modified Polyurethane", Journal of Polymer Science: PART A: Polymer Chemistry, vol. 40, pp. 486-495 (2002).

Chen, D., et. al. Amphiphilic Networks: 11. Biocompatibility and Controlled Drug Release of Poly[Isobutylene-co-2-(dimethylamino)Ethyl Methacrylate]. J. of Biomedical Materials Research, 23:1327-1342, 1989.

Chen, T. K., et. al. Glass Transition Behaviors of a Polyurethane Hard Segment based on 4, 4'- Diisocyanatodiphenylmethane and 1,4-Butanediol and the Calculation of Microdomain Composition. Macromolecules, 30:5068-5074, 1997.

Cho, J. C., et. al. Synthesis, Characterization, Properties, and Drug Release of Poly(Alkyl Methacrylate-B-Isobutylene-B-Alkyl Methacrylate). Biomacromolecules, 7:2997-3007, 2006.

Choi, T., et. al. Segmented Polyurethanes Derived from Novel Siloxane-Carbonate Soft Segments for Biomedical Applications. Journal of Polymer Science Part B: Polymer Physics, 49:865-872, 2011.

Christenson, E. M., et. al. Oxidative Mechanisms of Poly(Carbonate Urethane) and Poly(Ether Urethane) Biodegradation: In Vivo and In Vitro Correlations. J. Biomed. Mater. Res., 70A:245-255, 2004.

Claiborne, T. E., Slepian, M. J., Hossainy, S., & Bluestein, D. (2013). Polymeric trileaflet prosthetic heart valves: evolution and path to clinical reality. Expert Rev Med Devices., 9(6):577-594.

Communication in Cases for Which No Other Form is Applicable, issued in PCT/US2013/053448, dated Jul. 28, 2014, 1 page.

Cozzens, David et al. Long Term in Vitro Biostability of Segmented Polyisobutylene-Based Thermoplastic Polyurethanes. Journal of Biomedicals Materials Research Journal, Part A, 774-782, 2010.

De, Priyadarsi et al., "Carbocationic Polymerization of Isobutylene Using Methylaluminum Bromide Coinitiators: Synthesis of Bromoally Functional Polyisobutylene" Macromolecules, Oct. 2006, 39(2), 7527-7533.

De, Priyadarsi et al., "Relative Reactivity of C4 Olefins toward the Polyisobutylene Cation" Macromolecules 2006, 39, 6861-6870.

Erdodi, G., et al., "Polyisobutylene-Based Polyurethanes. III. Polyurethanes Containing PIB/PTMO Soft Co-Segments," J. Polym. Sci., Part A: Polym. Chem, 47:5278-5290 (2009).

Erdodi, G., et al., "Polyisobutylene-Based Polyurethanes. VI. Unprecedented Combination of Mechanical Properties and Oxidative/Hydrolytic Stability by H-Bond Acceptor Chain Extenders" J. Polym. Sci., Part A: Polym. Chem, 48:2361-2371 (2010).

Examination Report and Search Report for Chinese Application No. 201380042582.3, dated Dec. 4, 2015, consisting of 6 pages.

Extended European Search Report issued in EP appln. 16206626.0, dated Apr. 25, 2017, 8 pages.

Fan, L., et. al. The Absolute Calibration of a Small-Angle Scattering Instrument with a Laboratory X-ray Source. XIV International Conference on Small-Angle Scattering (SAS09), Journal of Physics: Conference Series 247, 11 pages, 2010.

Faust, R. et al., "Method to Prepare Block Copolymers by the Combination of Cationic and Anionic Polymerization", U.S. Appl. No. 12/225,905, filed Apr. 5, 2007.

Fischer, Stefan; et al. "Synthesis and Biological Evaluation of Bromo- and Fluorodanicalipin A." Angew. Chem. Int. Ed. 2016, 55, 2555-2558.

Gadkari A. et al., "Preparation and biocompatibility of Novel Polar-Nonpolar Networks. Osynthesis, Characterization and Histological-Bacterial Analysis of Mixed Polytetrahydrofuran-Polyisobutylene Networks", Polymer Bulletin, vol. 22, No. 1, Jul. 1, 1989, pp. 25-32.

Georgiou, Theoni K; et al. "Amphiphilic Model Conetworks of Polyisobutylene Methacrylate and 2-(Dimethylamino) ethyl Methacrylate Prepared by the Combination of Quasiliving Carbocationic and Group Transfer Polymerizations." Macromolecules 2007, 40, 2335-2343.

Giusti, Paolo et al., "Synthesis and Characterization of New potentially Hemocompatible Thermoplastic Elastomers", p. 371, Abstract.

Gunatillake, P. A., et. al. Synthesis and Characterization of a Series of Poly(alkylene carbonate) Macrodiols and the Effect of Their Structure on the Properties of Polyurethanes. Journal of Applied Polymer Science, 69:1621-1633, 1998.

Gunatillake, P.A. et al., "Poly(dimethylsiloxane)/Poly(hexamethylene oxide) Mixed Macrodiol Based Polyurethane Elastomers. I. Synthesis and Properties", Journal of Appl. Polym. Sci. 2000, 76, 2026-2040, © 2000

Gyor, M., et. al. Living Carbocationic Polymerization of Isobutylene with Blocked Bifunctional Initiators in the Presence of Di-tert-butylpyridine as a Proton Trap. J. of Macromolecular Science, Part A, Pure Appl. Chem., 29 (8):639-653, 1992.

H. Mach and P. Rath. "Highly Reactive Polyisobutene as a Component of a New Generation of Lubricant and Fuel Additives," Lubrication Science 11-2, Feb. 1999, pp. 175-185.

Hansen, Charles M. Hansen Solubility Parameters: A User's Handbook, 2nd ed. New York, CRC Press, Taylor & Francis Group, 2007, 546 pages.

Hernandez, et. al. R. Microstructural Organization of Three-Phase Polydimethylsiloxane-Based Segmented Polyurethanes. Macromolecules, 40:5441-5449, 2007.

Hernandez, R., et. al. A Comparison of Phase Organization of Model Segmented Polyurethanes with Different Intersegment Compatibilities. Macromolecules, 41:9767-9776, 2008.

Higashihara, T. et al., "Synthesis of Poly(isobutylene-block-methyl methacrylate) by a Novel Coupling Approach", Macromolecules, 39:5275-5279 (2006).

International Preliminary Report on Patentability and Written Opinion dated May 26, 2015 for International Application No. PCT/US2013/071170, entitled "High Strength Polyisobutylene Polyurethanes".

International Preliminary Report on Patentability issued in PCT/US2016/027294, dated Nov. 2, 2017, 7 pages.

International Preliminary Report on Patentability issued in PCT/US2016/067363, dated Jun. 28, 2018, 7 pages.

International Preliminary Report on Patentability, Chapter II, issued in PCT/US2006/035064, dated Sep. 12, 2007, 12 pages.

International Search Report and Written Opinion issued in PCT/US2006/013308, dated Aug. 25, 2006.

International Search Report and Written Opinion issued in PCT/US2006/035064, dated Jan. 23, 2007, 12 pages.

International Search Report and Written Opinion issued in PCT/US2007/007558, dated Sep. 20, 2007.

International Search Report and Written Opinion issued in PCT/US2007/008528, dated Oct. 2, 2007.

International Search Report and Written Opinion issued in PCT/US2007/012948, dated Nov. 28, 2007.

International Search Report and Written Opinion issued in PCT/US2010/028334, dated May 6, 2010, 12 pages.

International Search Report and Written Opinion issued in PCT/US2010/046072, dated Oct. 15, 2010, 10 pages.

International Search Report and Written Opinion issued in PCT/US2010/047633, dated Jun. 17, 2011, 12 pages.

International Search Report and Written Opinion issued in PCT/US2010/047703, dated Jun. 17, 2011, 12 pages.

* cited by examiner

PHOTOCROSSLINKED POLYMERS FOR ENHANCED DURABILITY

CROSS-REFERENCE TO RELATED APPLICATION

This application claims priority to Provisional Application No. 62/547,059, filed Aug. 17, 2017, which is herein incorporated by reference in its entirety.

TECHNICAL FIELD

The present disclosure relates to block copolymers. More specifically, the disclosure relates to cross-linked polyisobutylene-based polyurethanes, methods for making cross-linked polyisobutylene-based polyurethanes, and medical devices containing cross-linked polyisobutylene-based polyurethanes.

BACKGROUND

Polymeric materials are widely used in the field of implantable medical devices. For example, polymeric materials such as silicone rubber, polyurethane, and fluoropolymers are used as coating and/or insulating materials for medical leads, stents, and other devices. Polymeric materials may also be used for leaflets in replacement heart valves.

Block copolymers are polymeric materials made of alternating sections of polymerized monomers. Polyisobutylene-polyurethane block copolymers are polymeric materials that can have many desirable physical and mechanical properties, including thermal stability, chemical resistance, biocompatibility, and gas impermeability, among others.

SUMMARY

Example 1 is a block copolymer including a plurality of polymeric chains and a plurality of cross-linking compound residues linking together the plurality of polymeric chains. The plurality of polymeric chains forms a plurality of hard domains and a plurality of soft domains. Each polymeric chain includes a plurality of soft segments and a plurality of hard segments. The plurality of soft segments includes a polyisobutylene diol or diamine residue. The plurality of soft segments forms the plurality of soft domains. The plurality of hard segments including a diisocyanate residue. The plurality of hard segments forms the plurality of hard domains. The cross-linking compound residues link together the hard segments of the plurality of polymeric chains.

Example 2 is the block copolymer of Example 1, wherein the cross-linking compound residues are residues of a polyfunctional benzophenone.

Example 3 is the block copolymer of Example 2, wherein the polyfunctional benzophenone has a benzophenone functionality greater than 2 and less than 7.

Example 4 is the block copolymer of any of Examples 1-3, wherein the copolymer includes of a first portion and a second portion, the plurality of cross-linking compound residues disposed in the hard domains of the first portion, the second portion free of the plurality of cross-linking compound residues.

Example 5 is the block copolymer of Example 4, wherein the copolymer further includes a cross-linking compound, wherein the cross-linking compound is a precursor of the plurality of cross-linking compound residues, the cross-linking compound disposed in the hard domains of the second portion.

Example 6 is the block copolymer of any of Examples 1-5, wherein the diisocyanate residue includes 4,4'-methylene diphenyl diisocyanate residue.

Example 7 is the block copolymer of any of Examples 1-6, wherein the hard segments further include a chain extender residue.

Example 8 is the block copolymer of Example 7, wherein the chain extender residue is 1,4-butanediol residue.

Example 9 is the block copolymer of any of Examples 1-8, wherein the polyisobutylene diol or diamine residue is 5-tert-butyl-1,3-bis(1-methoxy-1-methylethyl)benzene.

Example 10 is the block copolymer of any of Examples 1-9, wherein the plurality of cross-linking compound residues link together at least a portion of the hard segments of the plurality of polymeric chains by covalent bonds.

Example 11 is a medical device including the block copolymer of any of Examples 1-10.

Example 12 is the medical device of Example 11, wherein the medical device is a heart valve.

Example 13 is a method of making a block copolymer. The method includes heating a mixture including soft segment components and hard segment components to an elevated temperature. The soft segment components include at least one polyisobutylene diol or diamine. The hard segment components include at least one diisocyanate. The method further includes maintaining the heated mixture for a time sufficient for the soft segment components and the hard segment components to form of a plurality of polymeric chains including soft segments and hard segments. The polymeric chains form a polymer matrix of soft domains including soft segments of the polymeric chains, and hard domains including hard segments of the polymeric chains. The method further includes adding a cross-linking compound to the polymer matrix, the cross-linking compound concentrating in the hard domains. The method further includes exposing at least a portion of the polymer matrix to radiation to activate the cross-linking compound. The activated cross-linking compound bonds to the polymeric chains in the exposed portion. The bonding is concentrated in the hard domains to form the block copolymer.

Example 14 is the method of Example 13, wherein the cross-linking compound is a polyfunctional benzophenone.

Example 15 is the method of either of Examples 13 or 14, wherein the entire polymer matrix is exposed to the radiation.

Example 16 is a block copolymer including a plurality of polymeric chains and a plurality of cross-linking compound residues linking together the plurality of polymeric chains. The plurality of polymeric chains forms a plurality of hard domains and a plurality of soft domains. Each polymeric chain includes a plurality of soft segments and a plurality of hard segments. The plurality of soft segments includes a polyisobutylene diol or diamine residue. The plurality of soft segments forms the plurality of soft domains. The plurality of hard segments including a diisocyanate residue. The plurality of hard segments forms the plurality of hard domains. The cross-linking compound residues link together the hard segments of the plurality of polymeric chains by covalent bonds.

Example 17 is the block copolymer of Example 16, wherein the cross-linking compound residues are residues of a polyfunctional benzophenone.

Example 18 is the block copolymer of Example 17, wherein the polyfunctional benzophenone has a benzophenone functionality greater than 2 and less than 7.

Example 19 is the block copolymer of any of Examples 16-18, wherein the copolymer includes of a first portion and a second portion, the plurality of cross-linking compound residues disposed in the hard domains of the first portion, the second portion free of the plurality of cross-linking compound residues.

Example 20 is the block copolymer of Example 19, wherein the copolymer further includes a cross-linking compound, wherein the cross-linking compound is a precursor of the plurality of cross-linking compound residues, the cross-linking compound disposed in the hard domains of the second portion.

Example 21 is the block copolymer of any of Examples 16-20, wherein the diisocyanate residue includes 4,4'-methylene diphenyl diisocyanate residue.

Example 22 is the block copolymer of Example 16, wherein the hard segments further include a chain extender residue.

Example 23 is the block copolymer of Example 22, wherein the chain extender residue is 1,4-butanediol residue.

Example 24 is a medical device including a block copolymer. The block copolymer includes a plurality of polymeric chains and a plurality of cross-linking compound residues linking together the plurality of polymeric chains. The plurality of polymeric chains forms a plurality of hard domains and a plurality of soft domains. Each polymeric chain includes a plurality of soft segments and a plurality of hard segments. The plurality of soft segments includes a polyisobutylene diol or diamine residue. The plurality of soft segments forms the plurality of soft domains. The plurality of hard segments including a diisocyanate residue. The plurality of hard segments forms the plurality of hard domains. The cross-linking compound residues link together the hard segments of the plurality of polymeric chains by covalent bonds.

Example 25 is the medical device of Example 24, wherein the cross-linking compound residues are residues of a polyfunctional benzophenone.

Example 26 is the medical device of Example 25, wherein the polyfunctional benzophenone has a benzophenone functionality greater than 2 and less than 7.

Example 27 is the medical device of any of Examples 24-26, wherein the copolymer includes of a first portion and a second portion, the plurality of cross-linking compound residues disposed in the hard domains of the first portion, the second portion free of the plurality of cross-linking compound residues.

Example 28 is the medical device of Example 27, wherein the copolymer further includes a cross-linking compound, wherein the cross-linking compound is a precursor of the plurality of cross-linking compound residues, the cross-linking compound disposed in the hard domains of the second portion.

Example 29 is the medical device of any of Examples 24-28, wherein the diisocyanate residue includes 4,4'-methylene diphenyl diisocyanate residue.

Example 30 is the medical device of any of Examples 24-29, wherein the hard segments further include a chain extender residue.

Example 31 is the medical device of Example 30, wherein the chain extender residue is 1,4-butanediol residue.

Example 32 is the medical device of any of Examples 24-31, wherein the medical device is a heart valve.

Example 33 is a method of making a block copolymer. The method includes heating a mixture including soft segment components and hard segment components to an elevated temperature. The soft segment components include at least one polyisobutylene diol or diamine. The hard segment components include at least one diisocyanate. The method further includes maintaining the heated mixture for a time sufficient for the soft segment components and the hard segment components to form of a plurality of polymeric chains including soft segments and hard segments. The polymeric chains form a polymer matrix of soft domains including soft segments of the polymeric chains, and hard domains including hard segments of the polymeric chains. The method further includes adding a cross-linking compound to the polymer matrix, the cross-linking compound concentrating in the hard domains. The method further includes exposing at least a portion of the polymer matrix to radiation to activate the cross-linking compound. The activated cross-linking compound covalently bonds to the polymeric chains in the exposed portion. The bonding is concentrated in the hard domains to form the block copolymer.

Example 34 is the method of Example 33, wherein the cross-linking compound is a polyfunctional benzophenone.

Example 35 is the method of either of Examples 33 or 34, wherein the entire polymer matrix is exposed to the radiation.

While multiple examples are disclosed, still other examples in accordance with this disclosure will become apparent to those skilled in the art from the following detailed description, which shows and describes illustrative embodiments. Accordingly, the drawings and detailed description are to be regarded as illustrative in nature and not restrictive.

Figure 1:
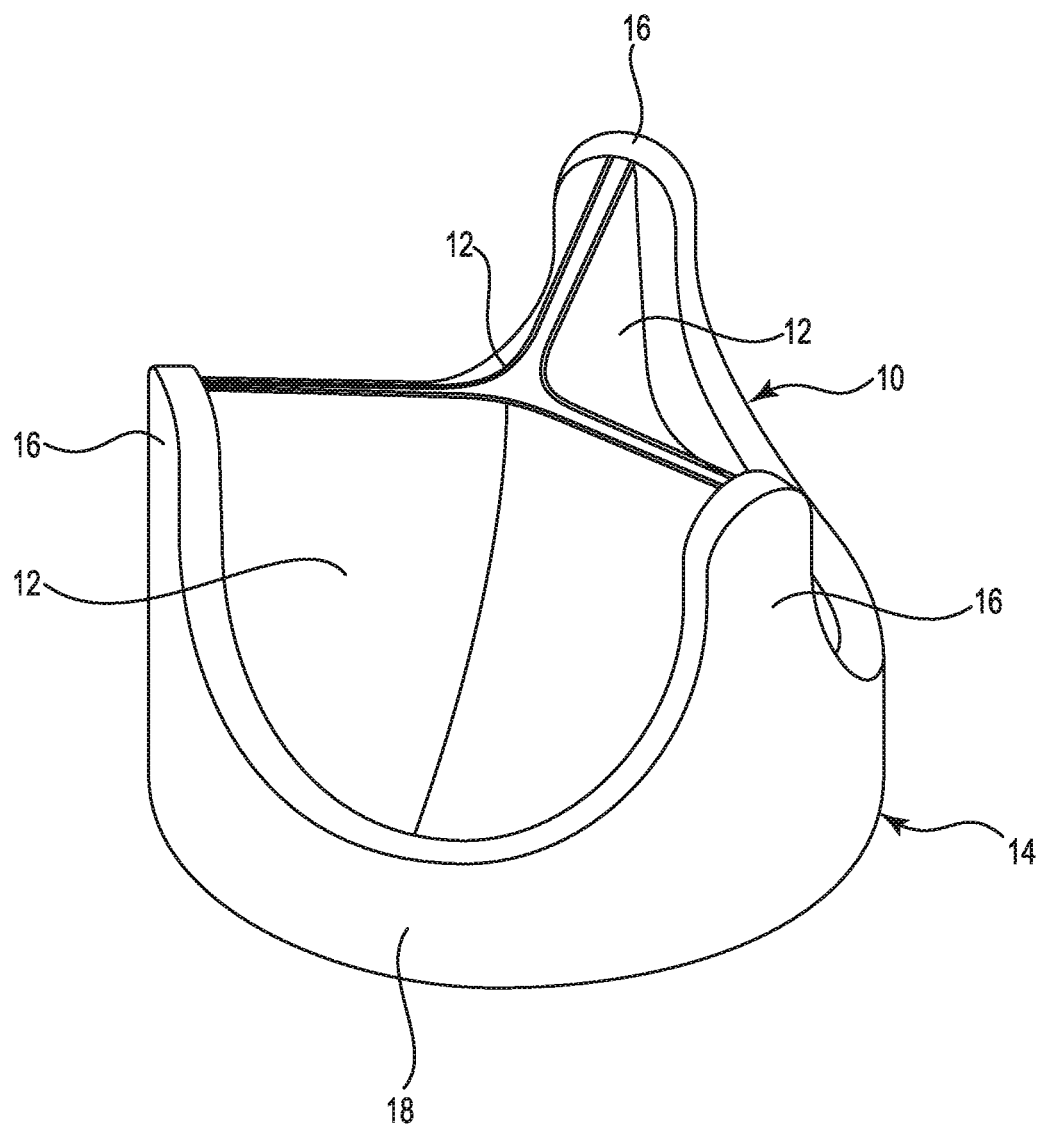
FIG. 1 is a perspective view of a heart valve in accordance with embodiments of this disclosure.

While this disclosure is amenable to various modifications and alternative forms, specific embodiments have been shown by way of example in the drawings and are described in detail below. The intention, however, is not to limit the disclosure to the particular embodiments described. On the contrary, this disclosure is intended to cover all modifications, equivalents, and alternatives falling within the scope of the disclosure as defined by the appended claims.

DETAILED DESCRIPTION

Medical devices can include synthetic polymers which substitute for natural tissues. For example, in some replacement heart valves, a synthetic polymer can substitute for the natural tissue forming the valve leaflets. The natural tissue includes collagen and elastin. Without wishing to be bound by any theory, it is believed that the combination of collagen and elastin permits the valve leaflets to move easily under low stress and then stiffen significantly when higher stresses are reached. This non-linear "strain stiffening" provides for a natural heart valve that is soft, efficient, and able to move with little stress at low stress levels, but stiffens at higher stress levels to reduce creep induced damage.

Polyisobutylene polyurethane (PIB-PUR) block copolymers are durable, biocompatible polymers suitable for a wide variety of medical applications. The PIB-PUR block copolymers are made of polymeric chains including hard segments and soft segments. The components making up the hard segments are more polar than the components making up the soft segments. As the PIB-PUR block copolymers are formed, there is a natural phase separation between the hard segment components and the soft segment components driven by associated hydrogen bonding and intermolecular forces arising from the polarity of the hard segment components. This self-organizing behavior can provide physical crosslinking of the bulk material, which may provide some of the advantageous properties of the PIB-PUR block copolymer.

In thermoplastic PIB-PUR block copolymers, hydrogen bonding and intermolecular forces act to organize the polymeric chains into a polymer matrix such that the hard segment components of adjacent polymeric chains are bonded together to form hard domains, leaving the soft segment components to form soft domains. The strength of the hydrogen bonding and intermolecular forces bonding the polymeric chains together in the hard domains is relatively weak, permitting the polymeric chains to separate from each other with the application of heat or stress, and then reconnect when the heat or stress is removed. Valve leaflets formed of thermoplastic PIB-PUR block copolymers can be soft and can efficiently move under stress due to the weak bonding. However, because of the weak bonding, thermoplastic PIB-PUR block copolymers can creep under stress as the polymer matrix is distorted by the breaking and reforming of the weak bonds, resulting in creep-induced damage to the leaflets. In some cases, the creep-induced damage can deform the leaflets enough to cause the valves to leak.

In thermoset PIB-PUR block copolymers, the polymeric chains are cross-linked to each other by covalent bonds. The covalent bonds can form all along the polymeric chains in the soft domains as well as the hard domains, resulting in a stiff polymer matrix. The strength of the covalent bonds is about three orders of magnitude greater than the strength of the bonds formed by hydrogen bonding and intermolecular forces. As a result, valve leaflets formed of thermoset PIB-PUR block copolymers my not creep under stress. However, thermoset PIB-PUR block copolymers are stiff and may not move easily under stress, so valve leaflets made formed of thermoset PIB-PUR block copolymers may be less efficient by requiring more energy to function. Thus, neither thermoplastic PIB-PUR block copolymers nor thermoset PIB-PUR block copolymers exhibit the desired non-linear strain stiffening found in some natural tissues, such as heart valve leaflets.

Embodiments of the present disclosure include PIB-PUR block copolymers that are soft and easily moved under low stresses, and stiffen significantly when higher stresses are reached. Such PIB-PUR block copolymers can exhibit the non-linear strain stiffening found in some natural tissues and can be used, for example, in leaflets in replacement heart valves to provide a more efficient and durable heart valve compared to other synthetic polymers.

FIG. 1 is a perspective view of a heart valve 10 in accordance with embodiments of this disclosure. As shown in FIG. 1, the heart valve 10 is a trileaflet heart valve including three valve leaflets 12 connected to a housing 14. The housing 14 includes three posts 16 extending from a stent structure 18 in what is a downstream direction when installed in a patient's heart (not shown). The stent structure 18 can be a circular ring configured to be implanted within the patient's heart. Each of the three valve leaflets 12 is connected to two of the three posts 16 and to the stent structure 18. In some embodiments, the three valve leaflets 12 and the housing 14 may be integrally formed of a PIB-PUR block copolymer according to embodiments described below. In such embodiments, the housing 14 may contain an interior skeleton (not shown) formed of a material more rigid than the block copolymer, and the valve leaflets 12 and the polymer portion of the housing 14 may be integrally formed around the interior skeleton. In other embodiments, the three valve leaflets 12 may be formed of the PIB-PUR block copolymer according to embodiments, and then attached to the housing 14. In such embodiments, the housing 14 may be formed of a material other than the block copolymer.

In use, the heart valve 10 can have a closed position, as shown in FIG. 1, and an open configuration (not shown). In the closed configuration, each of the three valve leaflets 12 have a concave curvature and are in contact with each other, but not attached to each other. When a blood pressure on a downstream side (same side as posts 16) is greater than an upstream side (opposite the downstream side), the three valve leaflets 12 are forced together by the blood pressure exerted against the concave curvature of the valve leaflets 12 to seal the heart valve 10 and prevent the flow of blood in the upstream direction. When the blood pressure on the upstream side is greater than the downstream side, the valve leaflets 12 are forced apart, forming the open configuration to permit blood to flow from the upstream side to the downstream side. The three valve leaflets 12 are easily and efficiently moved between the open configuration and the closed configuration because of soft nature of the PIB-PUR block copolymer. But when subjected to higher stresses which might otherwise distort the shape of the valve leaflets 12, the PIB-PUR block copolymer stiffens, protecting the three valve leaflets 12 from creep induced damage.

Although the embodiment describe above includes the PIB-PUR block copolymer according to embodiments described below incorporated into the heart valve 10, it is understood that the PIB-PUR block copolymer according to embodiments described below can be incorporated into any of a variety of medical devices which can be implanted or inserted into the body of a patient and which undergo significant amounts of dynamic stress. Example medical devices may include, without limitation: electrical leads and cables for rhythm management devices, artificial pericardium, aortic cuffs, and catheters, such as, for example, biliary drainage catheters.

Figure 2:
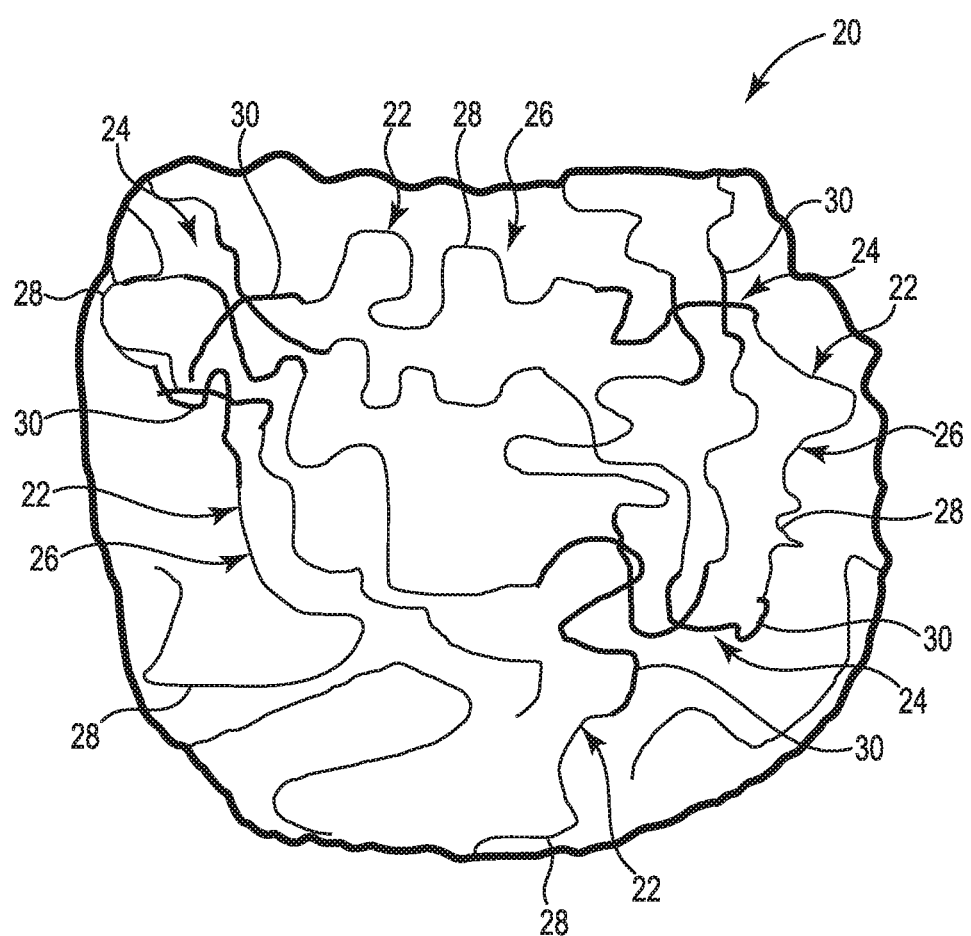
FIGS. 2-4 are schematic illustrations of the formation of a PIB-PUR block copolymer, according to embodiments of this disclosure.
Figure 3:
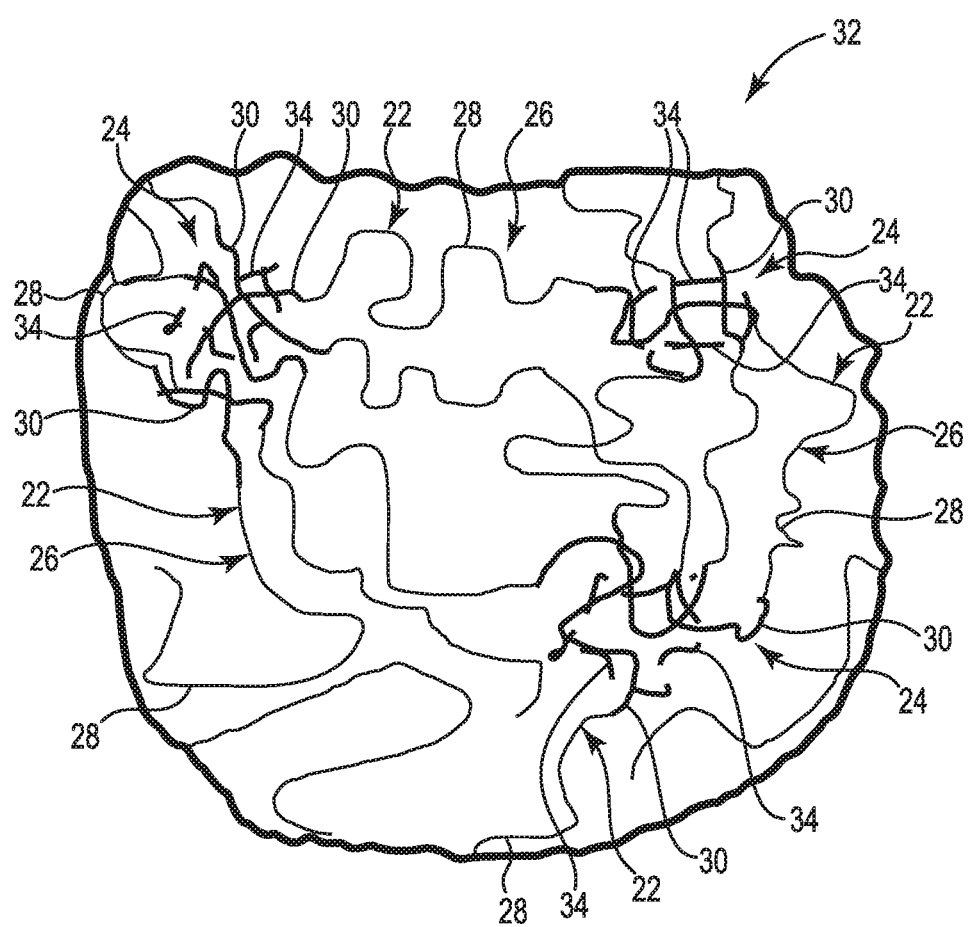
Figure 4:
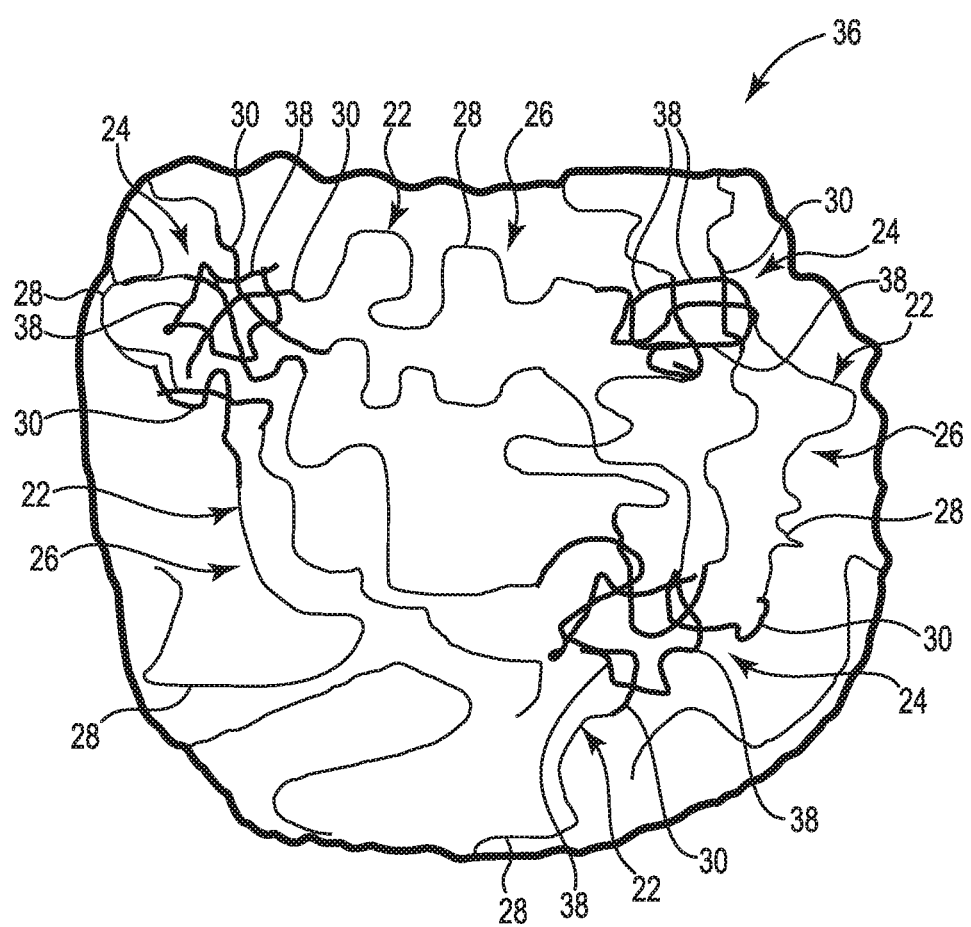

FIGS. 2-4 are schematic illustrations of the formation of a PIB-PUR block copolymer, according to embodiments of this disclosure. FIG. 2 shows a PIB-PUR block copolymer matrix 20 including a plurality of polymeric chains 22 forming a plurality of hard domains 24 and a plurality of soft domains 26. Each of the polymeric chains 22 can include one or more soft segments 28 and one or more hard segments 30. The hydrogen bonding and intermolecular forces of the hard segments 30 act to organize the plurality polymeric chains 22 into the PIB-PUR block copolymer matrix 20 such that the hard segments 30 of adjacent polymeric chains 22 are bonded together to form the plurality of hard domains 24, leaving the soft segments 28 to form the soft domains 26.

The soft segments 28 can be formed from a polyisobutylene diol or diamine, and thus include a residue of the polyisobutylene diol or diamine. For example, the polyisobutylene diol may be a telechelic polyisobutylene diol formed from by carbocationic polymerization beginning with a difunctional initiator compound, such as 5-tert-butyl-1,3-bis(1-methoxy-1-methylethyl)benzene (hindered dicumyl ether). The resulting compound may be a polyisobutylene diol according to Formula I:

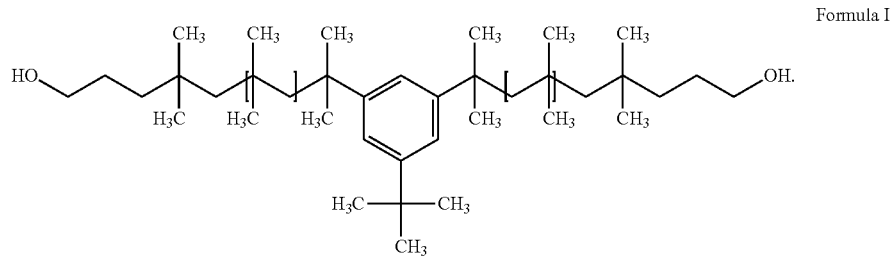

Formula I

Optionally, in some embodiments, the soft segments may additionally be formed from one or more polyether diols, and thus include a residue of the one or more polyether diols. Suitable optional polyether diols may include polytetramethylene oxide diol (PTMO diol), polyhexametheylene oxide diol (PHMO diol), polyoctamethylene oxide diol, and polydecamethylene oxide diol.

The hard segments 30 can be formed from polyfunctional isocyanates, such as diisocyanates, including both aliphatic and aromatic diisocyanates, and thus include a diisocyanate residue. Diisocyanates for use in forming the PIB-PUR block copolymer matrix 20 can include aromatic and non-aromatic (e.g., aliphatic) diisocyanates. Aromatic diisocyanates may be selected from suitable members of the following, among others: 4,4'-methylenediphenyl diisocyanate (MDI), 2,4'-methylenediphenyl diisocyanate (2,4-MDI), 2,4- and/or 2,6-toluene diisocyanate (TDI), 1,5-naphthalene diisocyanate (NDI), para-phenylene diisocyanate, 3,3'-tolidene-4,4'-diisocyanate and 3,3'-dimethyl-diphenylmethane-4,4'-diisocyanate. Non-aromatic diisocyanates may be selected from suitable members of the following, among others: 1,6-hexamethylene diisocyanate (HDI), 4,4'-dicyclohexylmethane diisocyanate (H12-MDI), 3-isocyanatomethyl-3,5,5-trimethylcyclohexyl isocyanate (isophorone diisocyanate or IPDI), cyclohexyl diisocyanate, and 2,2,4-trimethyl-1,6-hexamethylene diisocyanate (TMDI).

In some embodiments, the hard segments 30 may further include one or more optional chain extender residues. The chain extenders can increase the hard segment length, which can in turn results in a copolymer with a higher tensile modulus, lower elongation at break and/or increased strength. Chain extenders can be formed from aliphatic or aromatic diols, in which case a urethane bond is formed upon reaction with an isocyanate group. Chain extenders may be selected from suitable members of the following, among others: 1,4 cyclohexanedimethanol, alpha,omega-alkane diols such as ethylene glycol (1,2-ethane diol), 1,4-butanediol (BDO), and 1,6-hexanediol.

FIG. 3 shows a PIB-PUR block copolymer matrix 32. The PIB-PUR block copolymer matrix 32 can be identical to the PIB-PUR block copolymer matrix 20 of FIG. 2, except that it includes a cross-linking compound 34. The cross-linking compound 34 is a polyfunctional compound so that it is able to bond to at least two different polymeric chains 22 to cross-link the polymeric chains 22. The cross-linking compound 34 is more polar than the components making up the soft segments 28 and will have a greater affinity for the hard segments 30 than for the soft segments 28. The greater affinity of the cross-linking compound 34 for the hard segments 30 drives the cross-linking compound 34 to be disposed in the hard domains 24, near and amongst the hard segments 30 as the cross-linking compound 34 diffuses through the PIB-PUR block copolymer matrix 32. Thus, the cross-linking compound 34 will concentrate in the hard domains 24, as shown in FIG. 3.

FIG. 4 shows a PIB-PUR block copolymer matrix 36. The PIB-PUR block copolymer matrix 36 can be identical to the PIB-PUR block copolymer matrix 32 of FIG. 3, except that the PIB-PUR block copolymer matrix 36 has been exposed to radiation to activate the cross-linking compound 34 (FIG. 3). The radiation activates the cross-linking compound 34 by forming a radical that will readily form a covalent bond with the nearest carbon-hydrogen bond on the polymeric chains 22. The nearest carbon-hydrogen bond will most likely be in one of the hard segments 30, due the affinity of the cross-linking compound 34 for the hard segments 30. The cross-linking compound 34 can covalently bond to multiple polymeric chains 22 to form a cross-linking compound residue 38 linking together the polymeric chains 22 because the cross-linking compound 34 is polyfunctional. Thus, the cross-linking compound 34 is a precursor of the cross-linking compound residue 38. As shown in FIG. 4, the PIB-PUR block copolymer matrix 36 includes a plurality of cross-linking compound residues 38 linking together the plurality of polymeric chains 22. The cross-linking compound residues 38 link together the hard segments 30 of the plurality of polymeric chains 22 to form the PIB-PUR block copolymer matrix 36.

A PIB-PUR block copolymer having the PIB-PUR block copolymer matrix 36 shown in FIG. 4 can be soft and easily moved under low stresses due to the plurality of soft domains 26 which are not cross-linked. When higher stresses are reached as the soft domains 26 reach the extent of their elasticity, the plurality of hard domains 24 which are covalently cross-linked can cause the PIB-PUR block copolymer matrix 36 to stiffen significantly as they hold the polymeric chains 22 together. The strength of the covalently cross-linked hard domains 24 can reduce or prevent creep-induced damage. Thus, PIB-PUR block copolymer matrix 36 can exhibit the non-linear strain stiffening found in some natural tissues and can be used, for example, in the heart valve leaflets 12 in the heart valve 10 to provide a more efficient and durable heart valve 10 compared to other synthetic polymers.

Figure 5:
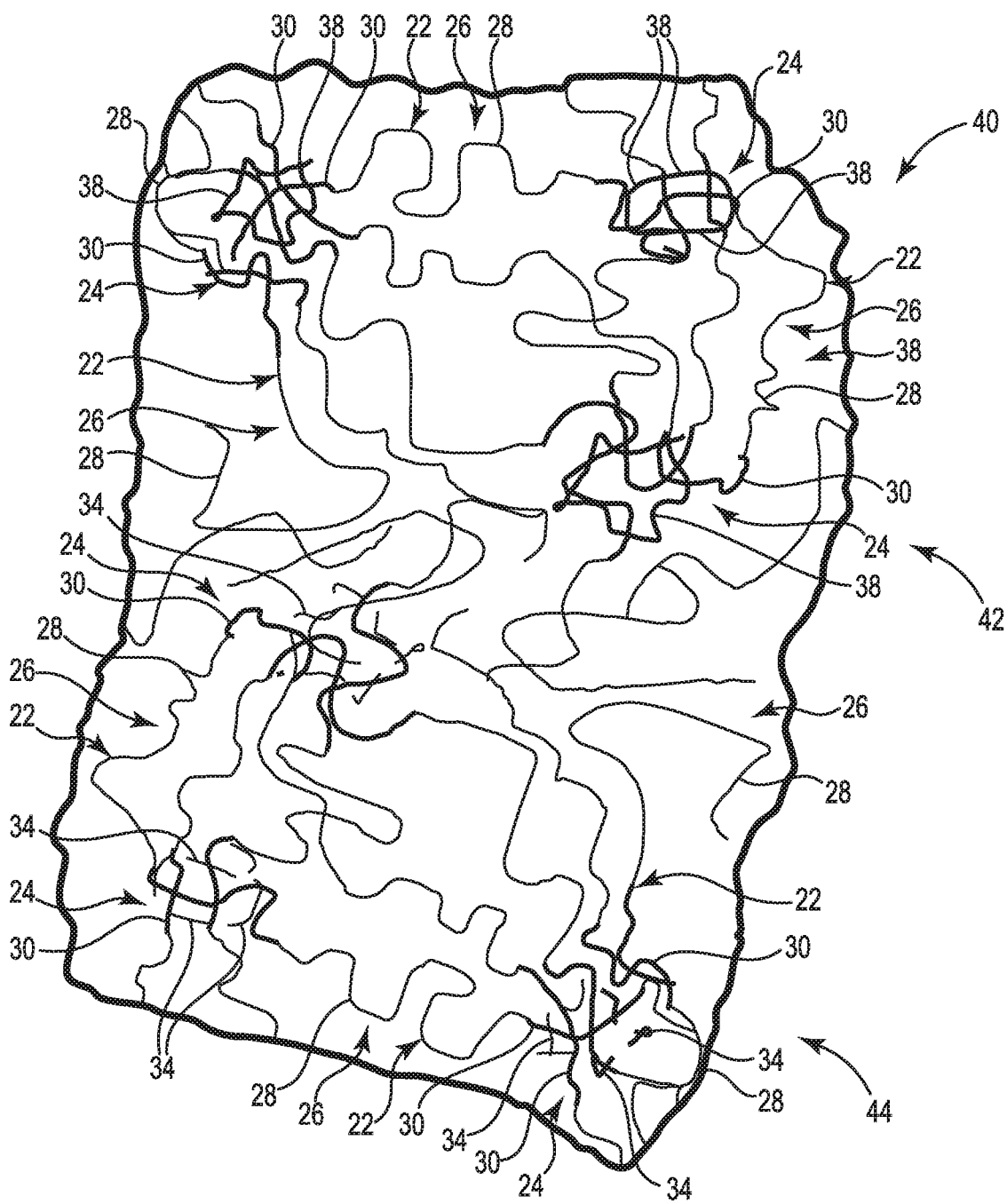
FIG. 5 is schematic illustration of another embodiment of a PIB-PUR block copolymer, according to embodiments of this disclosure.

FIG. 5 is schematic illustration of another embodiment of a PIB-PUR block copolymer, according to embodiments of this disclosure. FIG. 5 shows a PIB-PUR block copolymer matrix 40 that includes a first portion 42 and a second portion 44. The first portion 42 has been has been exposed to radiation to activate the cross-linking compound 34 to form the cross-linking compound residues 38 linking together the hard segments 30 of the plurality of polymeric chains 22. Thus, the first portion 42 is substantially similar to the PIB-PUR block copolymer matrix 36 (FIG. 4). The second portion 44 is substantially similar to the PIB-PUR block copolymer matrix 32 (FIG. 3) in that the second portion 44 has not been exposed to radiation, so the cross-linking compound 34 remains as a precursor concentrated in the hard domains 24 of the second portion 44. Thus, in the embodiment of FIG. 5, the cross-linking compound 34 has been selectively activated only in the first portion 42 to form the cross-linking compound residues 38 linking together the hard segments 30 of the plurality of polymeric chains 22 in the first portion 42 and the second portion 44 is free of the cross-linking residues 38. In other embodiments, the second portion 44 may not be completely free of the cross-linking residues 38 due to, for example, minor inadvertent or background exposure to radiation, but may be substantially free of the cross-linking compound residues 38. Substantially free means that less than 10%, less than 8%, less than 6%, less than 4%, less than 2%, less than 1%, less than 0.5%, or less than 0.1%, or less than any percentage between any two of the preceding percentages of the cross-linking compound 34 in the second portion 44 has been activated and formed the cross-linking residues 38. In this way, the stiffness of the PIB-PUR block copolymer matrix 40 can be varied to match stiffness variations found in natural tissues, such as, for example, the heart valve leaflets 12 (FIG. 1).

The plurality of hard domains 24 may include amorphous portions and crystalline portions. Until activated, the cross-linking compound 34 can act as a plasticizer in the hard domains 24 by interfering with the formation of the crystalline portions. However, due to its polarity, the cross-linking compound 34 may not drive the hard segments 30 apart. Once activated, the cross-linking compound 34 replaces the impermanent hydrogen bonds in the plurality of hard domains 24 with permanent covalent bonds. Thus, in some embodiments, the cross-linking compound 34 can act as a cross-linkable plasticizer.

In the embodiments described above in reference to FIGS. 3-5, all of the cross-linking compound 34 and/or all of the cross-linking compound residues 38 are shown disposed in the hard domains 24. However, it is understood that embodiments include block copolymers as describe above in which the cross-linking compound 34 and/or the cross-linking compound residues 38 are substantially disposed in the hard domains 24. For the purposes of this application, substantially disposed in the hard domains 24 means at least 90%, 92%, 94%, 96%, 98%, 99%, 99.5%, or 99.9% or at least any percentage between any two of the preceding percentages is disposed in the hard domains 24. These embodiments can form when some of the cross-linking compound 34 does not diffuse far enough to reach the hard domains 34. In such embodiments, the cross-linking compound 34 and/or the cross-linking compound residues 38 may be substantially disposed in the hard domains 24, and the remaining cross-linking compound 34 and/or the remaining cross-linking compound residues 38 may be disposed in the soft domains 26. In such embodiments, the remaining cross-linking compound residues 38 may link together some of the soft segments of the plurality of polymer chains 22. For the purposes of this application, concentrated in the hard domains 24 can include either or both of disposed in the hard domains 24 and substantially disposed in the hard domains 24.

Figure 6:
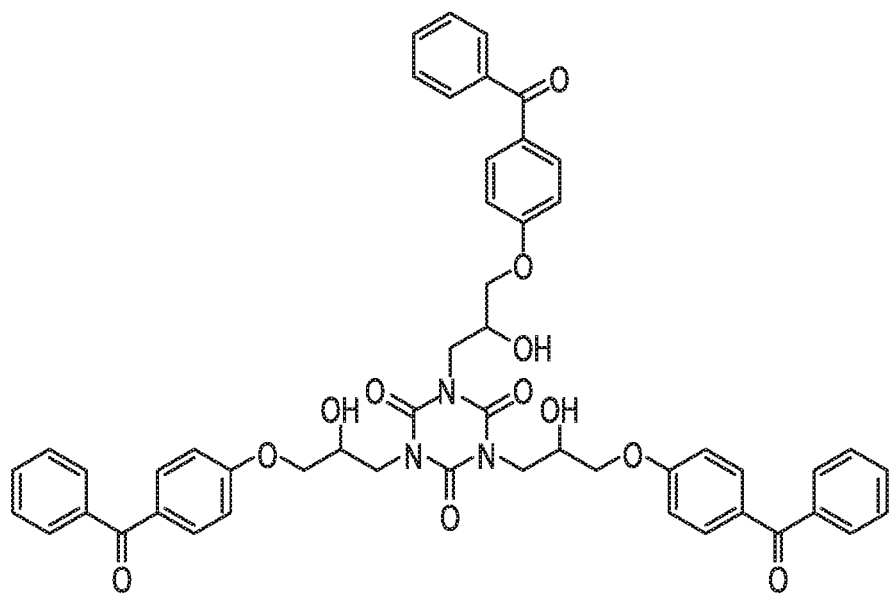
FIGS. 6-9 are chemical drawings illustrating examples of polyfunctional benzophenones suitable for forming PIB-PUR block copolymers, according to embodiments of this disclosure.
Figure 7:
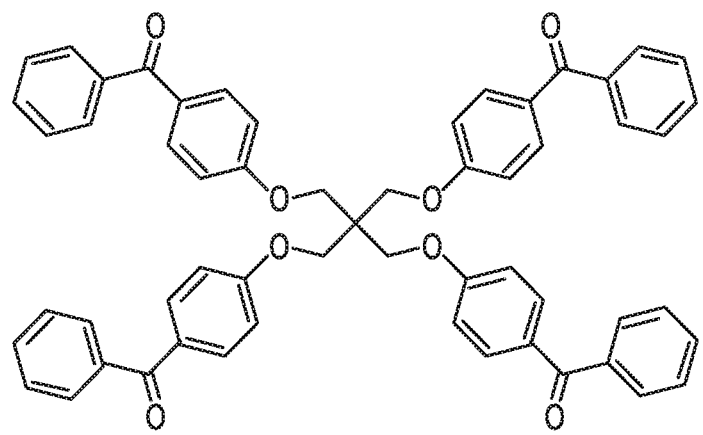
Figure 8:
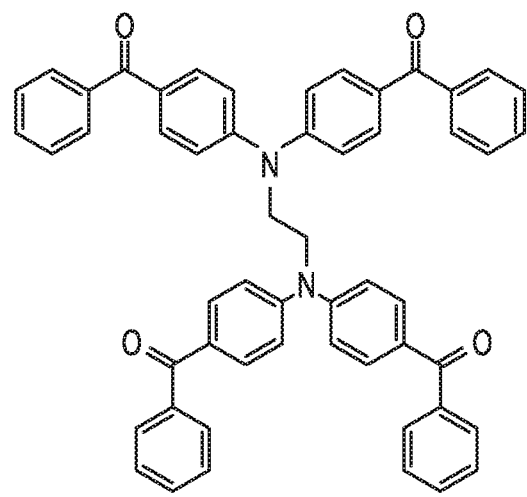
Figure 9:
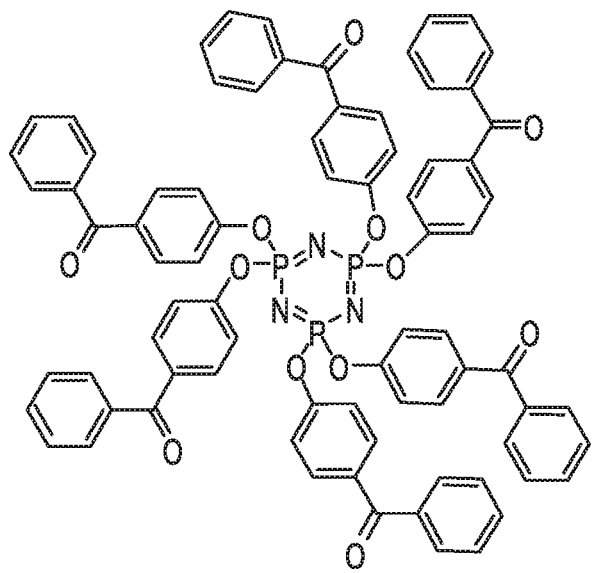

In some embodiments, the cross-linking compound 34 is a polyfunctional benzophenone. The polyfunctional benzophenones are aromatic rich and quite polar due to the benzophonones and the coordinating core of molecules. In some embodiments, the polyfunctional benzophenone can be a dibenzophenone with a functionality of 2, for example, 4,4"-oxy-di-benzophenone (CAS: 6966-89-8). In some other embodiments, the polyfunctional benzophenone can have a functionality greater than 2 and less than 7 to provide for greater cross-linking. FIGS. 6-9 are chemical drawings illustrating examples of polyfunctional benzophenones suitable for forming PIB-PUR block copolymers, according to embodiments of this disclosure. The polyfunctional benzophenone shown in FIG. 6 is 1,3,5-tris[3-(4-benzoylphenoxy)-2-hydroxypropyl]-1,3,5-triazine-2,4,6(1H,3H,5H)-trione (CAS #917248-81-8) which has a functionality of three, as it includes three benzophenone groups. The polyfunctional benzophenone shown in FIG. 7 is 1,1'-[[2,2-bis[(4-benzoylphenoxy)methyl]-1,3-propanediyl]bis(oxy-4,1-phenylene)]bis[1-phenylmethanone] (CAS #1579231-41-6) which has a functionality of four, as it includes four benzophenone groups. The polyfunctional benzophenone shown in FIG. 8 is 1,1',1'',1'''-[1,2-ethanediylbis(nitrilodi-4,1-phenylene)]tetrakis[1-phenylmethanone] (CAS #1622264-28-1) which also has a functionality of four, as it includes four benzophenone groups. The polyfunctional benzophenone shown in FIG. 9 is 2,2,4,4,6,6-hexakis(4-benzoylphenoxy)-2,2,4,4,6,6-hexahydro-1,3,5,2,4,6-triazatriphosphorine (CAS #84039-16-7) which has a functionality of six, as it includes six benzophenone groups.

Prior art initiator systems can have separate cross-linking initiators that generate free radicals which then must propagate to the cross-linking agents for successful cross-linking. Such systems can require maintaining an inert atmosphere to prevent oxygen from reacting with the free radicals before they get to the cross-linking agent. In embodiments in which the cross-linking compound 34 is a polyfunctional benzophenone, the cross-linking compound 34 acts as both cross-linking initiator and cross-linking agent. For such embodiments, there is no need to maintain an inert atmosphere because there is no need for a free radical produced by the initiator to propagate because the activated cross-linking compound 34 bonds directly to the polymeric chain 22.

The PIB-PUR block copolymer matrix 20 can be made by heating a mixture including soft segment components and hard segment components to an elevated temperature. An elevated temperature is any temperature above room temperature, such as 30° C., 40° C., 50° C., 60° C., 70° C., 80° C., 90° C., or 100° C., or any temperature between any of the preceding temperatures. The soft segment components can include at least one polyisobutylene diol or diamine, such as the polyisobutylene diol according to Formula I above. The hard segment components can include at least one diisocyanate, such as 4,4'-methylene diphenyl diisocyanate. In some embodiments, the hard segment components can further include a chain extender, for example, 1,4-butanediol. The heated mixture is maintained for a time sufficient for the soft segment components and the hard segment components to form of the plurality of polymeric chains 22 including the soft segments 28 and the hard segments 30, the polymeric chains self-organizing to form the PIB-PUR block copolymer matrix 20 of the soft domains 26 including primarily the soft segments 28 of the polymeric chains 22 and the hard domains 24 including primarily hard segments 30 of the polymeric chains 22, as shown in FIG. 2.

In some embodiments, a catalyst can be added to the mixture to increase the reaction rate and significantly reduce the time for substantial completion of the reaction. Tin(II) 2-ethylhexanoate and 2,6-dimethylpyridine are examples of such a catalyst.

Once the PIB-PUR block copolymer matrix 20 has formed, the cross-linking compound 34 can be added to the PIB-PUR block copolymer matrix 20. The cross-linking compound 34 can be, for example, any of the polyfunctional benzophenones described above. The cross-linking compound 34 has an affinity for the hard segments 30 due to its polarity and will diffuse through the polymeric chains 22 and concentrate in the hard domains 24 to form the PIB-PUR block copolymer matrix 32 as shown in FIG. 3.

In some embodiments, at least the first portion 42 can be exposed to radiation to activate the cross-linking compound 34, the cross-linking compound 34 bonding to the polymeric chains 22 in the first portion 42 to form the PIB-PUR block copolymer matrix 40 as shown in FIG. 5. In other embodiments, the entire PIB-PUR block copolymer matrix 32 can be exposed to radiation to activate the cross-linking compound 34, the cross-linking compound 34 bonding to the polymeric chains 22. In all embodiments, the bonding is concentrated in the hard domains 24.

In some embodiments, exposing the PIB-PUR block copolymer matrix 32, or the first portion 42 of the PIB-PUR block copolymer matrix 40, to radiation to activate the cross-linking compound 34 can include exposure to actinic photons, electron beams, or infrared sources. In some embodiments, actinic photons can be from an ultraviolet light source, which may, for example, be partially masked if only the first portion 42 is to be exposed. In some other embodiments, the infrared source can be from an infrared laser.

Various modifications and additions can be made to the embodiments discussed without departing from the scope of this disclosure. For example, while the embodiments described above refer to particular features, the scope of this disclosure also includes embodiments having different combinations of features and embodiments that do not include all of the described features. Accordingly, the scope of this disclosure is intended to embrace all such alternatives, modifications, and variations as fall within the scope of the claims, together with all equivalents thereof.

EXAMPLES

Manufacture of Photocrosslinked Polyisobutylene-Polyether-Polyurethane Block Copolymer In this Example, the manufacture of a photocrosslinked polyisobutylene-polyether-polyurethane block copolymer is demonstrated. 3 g of a polyisobutylene-polyether-polyurethane block copolymer was dissolved in 27 g of tetrahydrofuran (THF). The polyisobutylene-polyether-polyurethane block copolymer consisted of 55 wt. % polyisobutylene diol residue, 10 wt. % polytetramethylene oxide diol residue, and 35 wt. % of a stoichiometric ratio of 4,4'-methylenediphenyl diisocyanate and 1,4-butanediol. A 10 g aliquot of the 10 wt. % solution of polyisobutylene-polyether-polyurethane block copolymer was treated with a 1 g aliquot of an isopropanol solution of 0.1 wt. % 1,3,5-tris[3-(4-benzoylphenoxy)-2-hydroxypropyk]-1,3,5-triazine-2,4,6(1H,3H,5H)-trione and 0.9 wt. % 1-hydroxycyclohexyl phenyl ketone. The resulting solution was cast as a film in two aluminum pans, and placed in an oven under nitrogen gas flow at 50° C. until dry. One of the films was then treated using a Dymax UV curing chamber for 4 minutes, allowed to stand for 1 hour, flipped over, and treated on the other side in a similar fashion for 1 hour to cure, or crosslink the polyisobutylene-polyether-polyurethane block copolymer. The other film received no UV treatment.

The untreated film was submerged in THF and dissolved. The UV treated film was also submerged in THF, but showed no sign of dissolution, thus indicating that the film had been successfully covalently crosslinked and confirming that that the UV initiated crosslinking had worked as intended.

We claim:

1. A block copolymer comprising:
 a plurality of polymeric chains forming a plurality of hard domains and a plurality of soft domains, each polymeric chain including:
 a plurality of soft segments including a polyisobutylene diol or diamine residue, the plurality of soft segments forming the plurality of soft domains; and
 a plurality of hard segments including a diisocyanate residue, the plurality of hard segments forming the plurality of hard domains; and
 a plurality of cross-linking compound residues, the cross-linking compound residues linking together the plurality of polymeric chains, the cross-linking compound residues linking together the hard segments of the plurality of polymeric chains by covalent bonds, wherein the cross-linking compound residues are residues of a polyfunctional benzophenone.

2. The block copolymer of claim 1, wherein the polyfunctional benzophenone has a benzophenone functionality greater than 2 and less than 7.

3. The block copolymer of claim 1, wherein the copolymer includes of a first portion and a second portion, the plurality of cross-linking compound residues disposed in the hard domains of the first portion, the second portion free of the plurality of cross-linking compound residues.

4. The block copolymer of claim 3, wherein the copolymer further includes a cross-linking compound, wherein the cross-linking compound is a precursor of the plurality of cross-linking compound residues, the cross-linking compound disposed in the hard domains of the second portion.

5. The block copolymer of claim 1, wherein the diisocyanate residue includes 4,4'-methylene diphenyl diisocyanate residue.

6. The block copolymer of claim 1, wherein the hard segments further include a chain extender residue.

7. The block copolymer of claim 6, wherein the soft segments further include a residue of a polyether diol.

8. A medical device comprising:
 a block copolymer, the block copolymer including:
 a plurality of polymeric chains forming a plurality of hard domains and a plurality of soft domains, each polymeric chain including:
 a plurality of soft segments including a polyisobutylene diol or diamine residue, the plurality of soft segments forming the plurality of soft domains; and
 a plurality of hard segments including a diisocyanate residue, the plurality of hard segments forming the plurality of hard domains; and
 a plurality of cross-linking compound residues, the cross-linking compound residues linking together the plurality of polymeric chains, the cross-linking compound residues linking together the hard segments of the plurality of polymeric chains by covalent bonds, wherein the cross-linking compound residues are residues of a polyfunctional benzophenone.

9. The medical device of claim 8, wherein the polyfunctional benzophenone has a benzophenone functionality greater than 2 and less than 7.

10. The medical device of claim 8, wherein the copolymer includes of a first portion and a second portion, the plurality of cross-linking compound residues disposed in the hard domains of the first portion, the second portion free of the plurality of cross-linking compound residues.

11. The medical device of claim 10, wherein the copolymer further includes a cross-linking compound, wherein the cross-linking compound is a precursor of the plurality of cross-linking compound residues, the cross-linking compound disposed in the hard domains of the second portion.

12. The medical device of claim 8, wherein the diisocyanate residue includes 4,4'-methylene diphenyl diisocyanate residue.

13. The medical device of claim 8, wherein the hard segments further include a chain extender residue.

14. The medical device of claim 13, wherein the soft segments further include a residue of a polyether diol.

15. The medical device of claim 8, wherein the medical device is a heart valve.

16. A method of making a block copolymer, the method comprising:
heating a mixture including soft segment components and hard segment components to an elevated temperature, the soft segment components including at least one polyisobutylene diol or diamine, the hard segment components including at least one diisocyanate;
maintaining the heated mixture for a time sufficient for the soft segment components and the hard segment components to form of a plurality of polymeric chains including soft segments and hard segments, the polymeric chains forming a polymer matrix of soft domains including soft segments of the polymeric chains, and hard domains including hard segments of the polymeric chains;
adding a cross-linking compound to the polymer matrix, the cross-linking concentrating in the hard domains, wherein the cross-linking compound is a polyfunctional benzophenone;
exposing at least a portion of the polymer matrix to radiation to activate the cross-linking compound, the activated cross-linking compound covalently bonding to the polymeric chains in the exposed portion, the bonding concentrated in the hard domains to form the block copolymer.

17. The method of claim 16, wherein the entire polymer matrix is exposed to the radiation.

* * * * *